(12) United States Patent
Ma et al.

(10) Patent No.: US 11,660,575 B2
(45) Date of Patent: May 30, 2023

(54) REACTIVE INHIBITION OF PORE STRUCTURE COLLAPSE DURING PYROLYTIC FORMATION OF CARBON MOLECULAR SIEVES

(71) Applicants: ExxonMobil Technology and Engineering Company, Annandale, NJ (US); Georgia Tech Research Corporation, Atlanta, GA (US)

(72) Inventors: Yao Ma, Atlanta, GA (US); Melinda Jue, Atlanta, GA (US); Ryan Lively, Atlanta, GA (US); Dhaval Ajit Bhandari, Bridgewater, NJ (US)

(73) Assignees: ExxonMobil Technology and Engineering Company, Annandale, NJ (US); Georgia Tech Research Corporation, Atlanta, GA (US)

(*) Notice: Subject to any disclaimer, the term of this patent is extended or adjusted under 35 U.S.C. 154(b) by 422 days.

(21) Appl. No.: 16/717,788

(22) Filed: Dec. 17, 2019

(65) Prior Publication Data

US 2020/0206696 A1 Jul. 2, 2020

Related U.S. Application Data

(60) Provisional application No. 62/786,894, filed on Dec. 31, 2018.

(51) Int. Cl.
*C01B 32/336* (2017.01)
*C01B 32/306* (2017.01)
(Continued)

(52) U.S. Cl.
CPC ........... *B01D 71/021* (2013.01); *B01D 53/02* (2013.01); *B01D 53/228* (2013.01); *B01D 67/0044* (2013.01); *B01D 67/0067* (2013.01); *B01D 69/02* (2013.01); *B01J 20/20* (2013.01); *B01J 20/2808* (2013.01); *B01J 20/28033* (2013.01); *B01J 20/28059* (2013.01); *B01J 20/28061* (2013.01); *B01J 20/28064* (2013.01); *B01J 20/3078* (2013.01); *C01B 32/306* (2017.08); *C01B 32/336* (2017.08); *C07C 7/13* (2013.01); *C10G 25/05* (2013.01); *C10L 3/103* (2013.01);
(Continued)

(58) Field of Classification Search
None
See application file for complete search history.

(56) References Cited

U.S. PATENT DOCUMENTS

| 6,074,457 A | 6/2000 | Anthonis et al. |
| 2004/0050249 A1* | 3/2004 | Corbin .................. B01D 69/12 95/11 |

(Continued)

OTHER PUBLICATIONS

Hydrogen sulfide, Wikipedia, 1997, p. 2 para 1 [retrieved from the internet on Feb. 21, 2020 at https://en.wikipedia.org/wiki/Hydrogen_sulfide].

(Continued)

*Primary Examiner* — Tam M Nguyen
(74) *Attorney, Agent, or Firm* — Troutman Pepper Hamilton Sanders LLP; John A. Morrissett; Celeste K. Walker

(57) ABSTRACT

Disclosed herein are carbon molecular sieves and methods of making the same through the pyrolysis of a polymer precursor in the presence of a reactive gas stream including a hydrogen source.

22 Claims, 19 Drawing Sheets

(51) Int. Cl.
B01D 71/02 (2006.01)
B01D 67/00 (2006.01)
B01D 69/02 (2006.01)
B01D 53/02 (2006.01)
C07C 7/13 (2006.01)
C10L 3/10 (2006.01)
C10G 25/05 (2006.01)
B01J 20/20 (2006.01)
B01J 20/28 (2006.01)
B01J 20/30 (2006.01)
B01D 53/22 (2006.01)

(52) U.S. Cl.
CPC ............... *C10L 3/104* (2013.01); *C10L 3/105* (2013.01); *B01D 2253/102* (2013.01); *B01D 2253/306* (2013.01); *B01D 2253/308* (2013.01); *B01D 2256/245* (2013.01); *B01D 2257/702* (2013.01); *B01D 2325/02* (2013.01); *B01D 2325/20* (2013.01); *C01P 2002/72* (2013.01); *C01P 2006/12* (2013.01); *C01P 2006/16* (2013.01); *C10G 2300/107* (2013.01); *C10G 2300/1044* (2013.01); *C10G 2300/1051* (2013.01); *C10G 2300/1077* (2013.01); *C10G 2300/205* (2013.01); *C10G 2300/206* (2013.01); *C10G 2300/208* (2013.01); *C10G 2400/30* (2013.01); *C10L 2290/542* (2013.01)

(56) References Cited

U.S. PATENT DOCUMENTS

| | | | |
|---|---|---|---|
| 2013/0152793 A1* | 6/2013 | Bhuwania | B01D 69/08 423/447.4 |
| 2015/0290596 A1* | 10/2015 | Koros | B01D 71/021 96/14 |
| 2016/0184775 A1 | 6/2016 | Chevrel et al. | |
| 2016/0346740 A1* | 12/2016 | Koros | B01D 71/021 |
| 2016/0367948 A1 | 12/2016 | Song et al. | |
| 2019/0030491 A1* | 1/2019 | Zhang | B01D 67/0088 |
| 2019/0176090 A1* | 6/2019 | Lee | B01D 69/02 |
| 2021/0229030 A1* | 7/2021 | Vaughn | B01D 69/08 |
| 2022/0032237 A1* | 2/2022 | Ngamou | B01D 67/0048 |
| 2022/0080361 A1* | 3/2022 | Liu | B01D 67/0083 |

OTHER PUBLICATIONS

Hydrogenation, Wikipedia, 1996, para 1 [retrieved from the internet on Feb. 27, 2020 at https://en.wikipedia.org/wiki/Hydrogenation].
Kevlar, Wikipedia, 2000, p. 1 para 1, p. 4 para 1 [retrieved from the internet on Feb. 21, 2020 at https://en.wikipedia.org/wiki/Kevlar].
Why use a Tube Furnace?, Thermcraft, Feb. 27, 2020, p. 3 para 4 [retrieved from the internet on Feb. 27, 2020 at https://thermcraftinc.com/why-us-a-tube-furnace/].
Natural gas, Wiipedia, 2014, para 1 [retrieved from the internet on Feb. 24, 2020 at https://en.wikipedia.org/wiki/Natural_gas].
Petroleum naphtha, Wikipedia, 1993, para 1 [retrieved from the internet on Feb. 24, 2020 at https://en.wikipedia.org/wiki/Petroleum_naphtha].
International Search Report and Written Opinion dated Mar. 19, 2020, from the corresponding PCT Application No. PCT/US2019/066937.

* cited by examiner

REACTIVE INHIBITION OF PORE STRUCTURE COLLAPSE DURING PYROLYTIC FORMATION OF CARBON MOLECULAR SIEVES

CROSS REFERENCE TO RELATED APPLICATION

This application claims the benefit of U.S. Provisional Application No. 62/786,894, titled "REACTIVE INHIBITION OF PORE STRUCTURE COLLAPSE DURING PYROLYTIC FORMATION OF CARBON MOLECULAR SIEVES," filed Dec. 31, 2018, and which is fully incorporated by reference.

TECHNICAL FIELD

This disclosure relates generally to carbon molecular sieves and related methods for making the same. In particular, this disclosure relates to processes for inhibition of pore structure collapse during pyrolytic formation of a carbon molecular sieve.

BACKGROUND

Carbon molecular sieves (CMS) are a class of microporous carbonaceous materials derived from the pyrolytic decomposition of polymeric precursors. CMS membranes possess a turbostratic lamellar structure resulting in an amorphous and isotropic structure. On the one hand, over the short range, the carbon lamellae contain hybridized condensed hexagonal carbon sheets, which can align parallel to each other with random rotational angles. Essentially, the basic structural units are believed to comprise a kinetically trapped array of plates formed from strands created during aromatization and fragmentation of the precursor backbone. On the other hand, over the long range, these lamellae arrange randomly, bending and twisting to form an amorphous structure. This bimodal pore size distribution with larger micropores interconnected by smaller ultramicropores derives from packing imperfections of the carbon sheets. The ultramicropores enable molecular sieving, while the micropores provide abundant sorption sites. This combination allows CMS membranes to realize both high permeability and high selectivity simultaneously, which is attractive for separations. Moreover, CMS membranes have the ability to withstand high transmembrane pressure when fabricated in the form of asymmetric hollow fibers and exhibit chemical and thermal stability.

The molecular sieving performance of CMS can be determined by their microporous structures, which can be controlled by the polymer precursor and the pyrolysis conditions. Prior arts tune the CMS microporous structure by optimizing temperature profiles, choosing different inert gas environment and dosing oxygen molecules of certain concentration. Generally, higher pyrolysis temperature results in CMS with reduced pore sizes, which increases selectivity with a sacrifice of productivity. The effect of temperature on CMS structure is common for various types of polymer precursors, such as polyimide, fluorine-containing polymers, spiro polymers, etc. Inert gas (argon, helium and carbon dioxide) purging during pyrolysis leads to CMS membranes with higher productivity and lower selectivity compared with vacuum pyrolysis, since the enhanced heat and mass transfer facilitate the degradation process. Oxygen of suitable concentration in the pyrolysis atmosphere have also been used to reduce the pore sizes.

SUMMARY

Disclosed herein are processes for inhibiting pore structure collapse during pyrolytic formation of a carbon molecular sieves ("CMS") comprising providing a polymer precursor, heating the polymer precursor in a chamber to at least a temperature at which the polymer precursor is pyrolyzed, and flowing a reactive gas stream through the chamber during the heating. In some embodiments, the carbon molecular sieve is a membrane, adsorbent, catalyst, or a filter.

In some embodiments, the reactive gas stream includes a source of hydrogen. In some embodiments, the reactive gas stream includes $H_2$. In some embodiments, the $H_2$ is produced in-situ by combining hydrogen and a hydrocarbon in an autothermal or steam methane reforming type process.

In some embodiments, the polymer precursor is a film, hollow fiber, tube, or disc. In some embodiments, the polymer precursor comprises a rigid polymer. In some embodiments, the polymer precursor comprises a rigid, microporous polymer. In some embodiments, the rigid microporous polymer is a polymer of intrinsic microporosity selected from the group consisting of PIM-1, PIM-7, PIM-8, PIM-9, KAUST-PI-1, PIM-BADAS-1, PIM-DUCKY-1, PIM-Tz$_{25}$, PIM-DUCKY-2, PIM-BADAS-2, and PIM-SA-DAS.

In some embodiments, the reactive gas stream further comprises an inert gas selected from the group consisting of argon, neon, $N_2$, helium, and $CO_2$. In some embodiments, the reactive gas stream comprises $H_2$ and argon.

In some embodiments, the temperature of the pyrolysis of the polymer precursor film is from 500° C. to 1100° C.

In some embodiments, the $H_2$ is in a concentration of from 1 ppm to 4 vol. % of the reactive gas stream. In some embodiments, an inert gas stream flows through the chamber during the heating, wherein the inert gas stream comprises argon, and wherein flow rate of the inert gas stream is different from flow rate of the reactive gas stream.

Also disclosed herein are processes for controlling the pore structure of a carbon molecular sieve membrane comprising the steps of providing a polymer precursor, heating the polymer precursor in a chamber to at least a temperature at which the polymer precursor is pyrolyzed, and flowing a reactive gas stream through the chamber during the heating, wherein the reactive gas stream includes $H_2$.

In some embodiments, the polymer precursor comprises PIM-1. In some embodiments, the reactive gas stream further comprises an inert gas selected from a group consisting of argon, neon, $N_2$, helium, and $CO_2$. In some embodiments, the reactive gas stream comprises $H_2$ and argon.

In some embodiments, the temperature of the pyrolysis of the polymer precursor film is from 500° C. to 1100° C.

In some embodiments, the $H_2$ is in a concentration of from 1 ppm to 4 vol. % in the reactive gas stream.

In some embodiments, ramp rate of the process is from 0.1° C./min to 200° C./min.

In some embodiments, cool down rate of the process is from 0.1° C./min to 200° C./min.

In some embodiments, the reactive gas stream reacts with the polymer precursor to form $H_2O$ during pyrolysis.

In some embodiments, an inert gas stream flows through the chamber during the heating, wherein the inert gas stream comprises argon, and wherein flow rate of the inert gas stream is different from flow rate of the reactive gas stream.

In some embodiments, the chamber comprises a fume hood comprising a tubular furnace, a quartz tube disposed at least partially inside of the tubular furnace, a mesh plate support disposed inside of the quartz tube, and the polymer precursor film is disposed on the mesh plate support.

In some embodiments, the reactive pyrolysis method selectively targets the ultra-micropores while leaving the micropores relatively unchanged.

In some embodiments, the diffusion selectivity of the polymer precursor is enhanced while the sorption selectivity of the polymer precursor is essentially unchanged.

Also disclosed herein are carbon molecular sieve membranes produced according to the above-mentioned processes.

In some embodiments, the carbon molecular sieve membranes include ultra-micropores from 5 Å to 20 Å.

In some embodiments, the carbon molecular sieve membranes included a $sp^3/sp^2$ hybridized carbon ratio in the membrane from 0.10 to 1.0.

In some embodiments, the carbon molecular sieve membranes have a surface area from 2 $m^2/g$ to 1000 $m^2/g$.

In some embodiments, the carbon molecular sieve membranes have a p-xylene permeability fourteen times larger than a p-xylene permeability of a membrane prepared without $H_2$ during the heating.

In some embodiments, the carbon molecular sieve membranes have a p-xylene permeability of from $$8.5 \times 10^{-15} \frac{mol \times m}{m^2 \times s \times Pa} \text{ to } 8.5 \times 10^{-13} \frac{mol \times m}{m^2 \times s \times Pa}.$$

In some embodiments, a module comprising a plurality of carbon molecular sieves and used as an adsorbent bed or a membrane bed. In some embodiments, the adsorbent bed and the membrane bed are used for gas and vapor separations, aqueous separations, organic separations, and hydrocarbon separations.

Also disclosed herein are processes for performing a separation on a feed stream, comprising the module, wherein the feed stream comprises a first component and a second component, to form a permeate stream enriched in the first component and a retentate stream depleted in the first component. In some embodiments, the feed stream comprises the first component in concentration range of 1 wt. % to 99 wt. %.

In some embodiments, the feed stream is a natural gas stream, the permeate stream is enriched in the first component including at least one of $CO_2$, $H_2S$, $H_2O$, and He, and the retentate stream is enriched in the second component including at least one of $CH_4$ and $N_2$. In other embodiments, the feed stream comprises a $C_8$ aromatics stream, the permeate stream is enriched in the first component including at least one of benzene and p-xylene, and the retentate stream that is enriched in the second component including at least one of ethyl benzene, o-xylene and m-xylene. In some embodiments, the feed stream comprises a virgin naphtha stream (initial boiling point (IBP)-380° F.), the permeate stream is enriched in the first component including at least one of n-paraffins and aromatics, and the retentate stream is enriched in the second component including at least one of iso-paraffins and cyclo-paraffins. In some embodiments, the feed stream comprises a whole crude stream, the permeate stream is enriched in the first component including at least one of naphtha (IBP-380° F.) and kerosene fractions (380-530° F.), and the retentate stream that is enriched in the second component including at least one of the remaining fractions (530° F.+). In other embodiments, the feed stream includes a heavy hydrocarbon stream having bitumen, atmospheric resid, vacuum resid, steam cracker tar, and/or fluid catalytic cracker main column bottom, the permeate stream is enriched in the first component including at least one of saturates and/or 3– ring aromatics, and the retentate stream enriched in the second component including at least one of 3+ ring aromatics, asphaltenes, metals, and/or micro-carbon residue.

Also disclosed herein are modules comprising a plurality of carbon molecular sieve produced according to the above-mentioned processes and used as adsorbent beds or membrane beds.

In some embodiments, the adsorbent beds and the membrane beds are used for gas and vapor separations, aqueous separations, organic separations, and hydrocarbon separations.

BRIEF DESCRIPTION OF THE DRAWINGS

Reference will now be made to the accompanying figures, which are not necessarily drawn to scale, and wherein.

DETAILED DESCRIPTION

Figure 1:
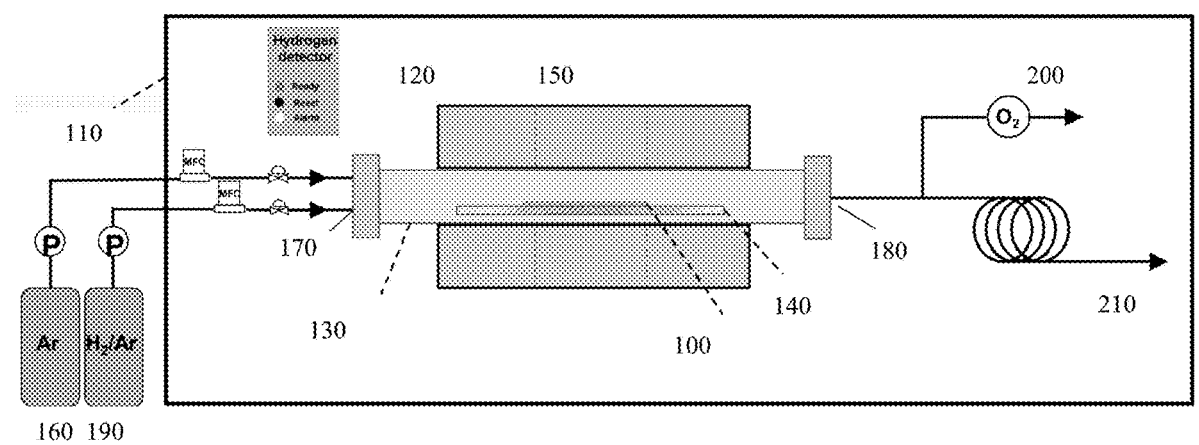
FIG. 1 depicts an embodiment of pyrolysis process disclosed herein, not necessarily drawn to scale.

Although some embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the embodiments, specific terminology will be resorted to for the sake of clarity.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The molecular sieving performance of CMS is determined by their microporous structures, which are controlled by the polymer precursor and the pyrolysis conditions. Known processes tune the CMS microporous structure by optimizing temperature profiles, choosing different inert gas environments and dosing oxygen molecules of certain concentration. Generally, higher pyrolysis temperature results in CMS membranes with reduced pore sizes, which increases selectivity with a sacrifice of productivity. The effect of temperature on CMS structure is common for various types of polymer precursors, such as polyimide, fluorine-containing polymers, spiro polymers, etc. Inert gas (e.g., argon, helium and carbon dioxide) purging during pyrolysis leads to CMS membranes with higher productivity and lower selectivity compared with vacuum pyrolysis, since the enhanced heat and mass transfer facilitate the degradation process. Oxygen of suitable concentration in the pyrolysis atmosphere have also been used to reduce the pore sizes.

The methods presented herein provide a novel route to manipulate the microporous structure of CMS membranes. For the first time, a reactive gas is introduced into the inert pyrolysis atmosphere. Here the gas is selected to be hydrogen or a source of hydrogen. According to Le Chatelier's principle, the presence of hydrogen hypothetically favors the formation of more twisted carbon strains and inhibits the consolidation of lateral adjacent stands, which results in larger ultramicropores. Some prior arts utilize carbon dioxide as inert pyrolysis atmosphere, which could also influence the resulting structure according to Le Chatelier principle. However, under high temperatures (e.g., 800° C.), carbon dioxide could be oxidative and result in CMS with highly open pores, which is nonselective to guest molecules. The introduction of reactive gas component (e.g. hydrogen) in the pyrolysis environment broadens the tunability range.

Disclosed herein are carbon molecular sieves and methods of making the same. Also disclosed herein are processes for inhibition of pore structure collapse during pyrolytic formation of a carbon molecular sieve including providing a polymer precursor, heating the polymer precursor in a chamber to at least a temperature at which the polymer precursor is pyrolyzed, and flowing a reactive gas stream through the chamber during the heating. In some embodiments, the first reactive gas stream includes $H_2$. The resulting $H_2$ assisted carbon molecular sieve have controlled pore structure and when used as a membrane exhibit good performance as ultrapermeable separation membranes. The manufacturing process enables an increase in p-xylene ideal permeability by 15 times when compared to carbon molecular sieves pyrolyzed under a pure argon atmosphere.

In a first aspect, FIG. 1 depicts an exemplary embodiment of a pyrolysis process in accordance with the present disclosure. It includes heating the polymer precursor 100 in a chamber to at least a temperature at which the polymer precursor is pyrolyzed and flowing a first reactive gas stream through the chamber during the heating. FIG. 1 shows a chamber including a fume hood 110. The fume hood can include a tubular furnace 120, a quartz tube 130 disposed at least partially inside of the tubular furnace 120, a mesh plate support 140 disposed inside of the quartz tube 130, and the polymer precursor 100 disposed on the mesh plate support 140. In some embodiments, the tubular furnace 120 can further include three zones of heating 150. Each zone can be controlled by its own thermocouple independently connected each heating zone. In this type of furnace, the tube is substantially centered such that the precursor polymer is within the heating zones. As further shown in FIG. 1, a reactive gas stream 190 including a hydrogen source and argon can be fed into the quartz tube 130 of the furnace 120. The quartz tube 130 can include an inlet 170 and an outlet 180. In some embodiments, a separate, inert gas stream 160 including argon can also be fed into the inlet 170 of the quartz tube 130 of the furnace 120. The inert gas in both the reactive gas stream and the inert gas stream can temper the effect of reactive gas so the pores are not over-engineered. In some embodiments, the inert gas in both the reactive gas stream and the inert gas stream can be selected from a group consisting of argon, neon, $N_2$, helium, and $CO_2$. In lieu of the quartz tube, any other similar chemically inert apparatus that can survive the pyrolysis conditions can be used. In still some embodiments, the fume hood can further include an $O_2$ detector 200 and/or a vent 210 for exhausting the reactive and inert gas streams, downstream the outlet of the quartz tube. In some embodiments, the inert gas stream is fed to the quartz tube at a different flow rate ratio than the reactive gas stream.

In some embodiments, the reactive gas stream source of hydrogen can include $H_2$. In some embodiments, the reactive gas stream is a pure $H_2$ stream. In some embodiments, the $H_2$ is in a concentration of from 1 ppm to 4 vol. % in the reactive gas stream (e.g., 10 ppm, 100 ppm, 1000 ppm, 1 vol. %, 2 vol. %, 3 vol. %). It is to be noted that each of the instant example disclosures capped the $H_2$ concentration at 4 vol. % for safety concerns, but higher $H_2$ concentrations are also contemplated. During the pyrolysis process, the existence of $H_2$ inhibits the pore structure collapse for the resulting CMS materials. The $H_2$ concentration can be selected to obtain a desired molecule permeance or permselectivity.

The pyrolysis typically follows the heating step. The polymer precursor is carbonized to a specific structural morphology and carbon composition by controlling the heating protocol with three critical variables: temperature set points in each heating zone, rate at which these temperatures set points are reached ("ramp"), and the amount of time maintained at these set points ("soak"). In some embodiments, ramp rate of the process is from 0.1° C./min to 200° C./min (e.g., 10° C./min, 2° C./min, 50° C./min, 75° C./min, 100° C./min, 125° C./min, 150° C./min, 175° C./min). The pyrolysis is generally performed with soak times ranging from several minutes to several hours (e.g. 30 min, 1 hr, 2 hrs, 4 hrs, 6 hrs, 8 hrs, 10 hrs, 12 hrs, 14 hrs, 16 hrs, 18 hrs, 20 hrs, 22 hrs, 24 hrs). Generally, the pyrolysis results in an amorphous material that is 80 wt. % or greater carbon and possesses a distribution of micropore dimensions with only short-range order of specific pore sizes.

The pyrolysis can be generally affected in a wide range of temperatures, from the decomposition temperature of the carbonaceous material to the graphitization temperature. In some embodiments, the pyrolysis temperature can vary in each heating zone from 500° C. to 1100° C. In some embodiments, the pyrolysis temperature in each and any of the zones of heating can range from 500° C. to 1300° C. (e.g., 450° C., 550° C., 600° C., 650° C., 700° C., 750° C., 850° C., 900° C., 950° C., 1000° C., 1050° C., 1150° C., 1200° C., 1250° C.). The pyrolysis temperature can be selected to obtain a desired molecule permeance or permselectivity.

Any suitable polymer precursor can be used that permits selective passage of the desired chemicals to be separated, for example xylene isomer separations. For adequate scalability of the production of carbon molecular sieves, the polymer precursor can be in the form of a film, fiber, hollow fiber, tube, powder or disc, monolith, pellet. The polymer can be coated onto a pyrolysis stable support such as on a metal, ceramic support or could be bound together with a binder such as clay, silica, alumina etc. In some embodiments, the polymer precursor comprises a rigid polymer. In some embodiments, the polymer precursor comprises a rigid, microporous polymer. A polymer powder may be converted into a polymer film for use in the pyrolysis process. The resulting CMS have a certain pore size and function as molecular sieves.

The carbon molecular sieve are ideally produced by the controlled pyrolysis of a suitable powder or film or fiber or hollow fiber of polymeric material. The polymeric powders can be formed by example, by milling a polyimide polymer using conventional methodology. Alternatively, polymeric films can be formed by solution casting a polyimide solution using conventional methodology, e.g., casting on a flat glass surface with a variable thickness polymer film applicator. Suitable polyimides can be formed, for example, by reacting suitable dianhydrides with diamines. In some embodiments, an aromatic polyimide resin is used to form a flat film. Virtually any powder size can be used, so long as the pyrolyzed material can be milled to the desired size. Suitable particle sizes for the powder range from 10 microns to 500 microns, although thicker or thinner particles can be used. Polymer films of desired thickness and area can be cut into desired sections and then pyrolyzed. Suitable film thicknesses range from 0.001 inch to 0.003 inch, e.g., 0.002 inch, although thicker or thinner films can be used.

Examples of suitable polymers include substituted or unsubstituted polymers and may be selected from polysulfones; poly(styrenes), including styrene-containing copolymers such as acrylonitrilestyrene copolymers, styrene-butadiene copolymers and styrene-vinylbenzylhalide copolymers; polycarbonates; cellulosic polymers, such as cellulose acetate-butyrate, cellulose propionate, ethyl cellulose, methyl cellulose, nitrocellulose, etc.; polyamides and polyimides, including aryl polyamides and aryl polyimides; polyethers; polyetherimides; polyetherketones; poly(arylene oxides) such as poly(phenylene oxide) and poly(xylene oxide); poly(esteramide-diisocyanate); polyurethanes; polyesters (including polyarylates), such as poly(ethylene terephthalate), poly(alkyl methacrylates), poly(acrylates), poly (phenylene terephthalate), etc.; polypyrrolones; polysulfides; polymers from monomers having alpha-olefinic unsaturation other than mentioned above such as poly (ethylene), poly(propylene), poly(butene-1), poly(4-methyl pentene-1), polyvinyls, e.g., poly(vinyl chloride), poly(vinyl fluoride), poly(vinylidene chloride), poly(vinylidene fluoride), poly(vinyl alcohol), poly(vinyl esters) such as poly(vinyl acetate) and poly(vinyl propionate), poly(vinyl pyridines), poly(vinyl pyrrolidones), poly(vinyl ethers), poly(vinyl ketones), poly(vinyl aldehydes) such as poly(vinyl formal) and poly(vinyl butyral), poly(vinyl amides), poly(vinyl amines), poly(vinyl urethanes), poly (vinyl ureas), poly(vinyl phosphates), and poly(vinyl sulfates); polyallyls; poly(benzobenzimidazole); polyhydrazides; polyoxadiazoles; polytriazoles; poly (benzimidazole); polycarbodiimides; polyphosphazines; etc., and interpolymers, including block interpolymers containing repeating units from the above such as terpolymers of acrylonitrile-vinyl bromide-sodium salt of para-sulfophenylmethallyl ethers; and grafts and blends containing any of the foregoing. Typical substituents providing substituted polymers include halogens such as fluorine, chlorine and bromine; hydroxyl groups; lower alkyl groups; lower alkoxy groups; monocyclic aryl; lower acyl groups and the like. In some embodiments, the suitable polymer precursor can be a polymer of intrinsic microporosity selected from, but not limited to, PIM-1, PIM-7, PIM-8, PIM-9, KAUST-PI-1, PIM-BADAS-1, PIM-DUCKY-1, PIM-Tz$_{25}$, PIM-DUCKY-2, PIM-BADAS-2, and PIM-SADAS, the structures for same in accordance with the chart below.

| Rigid microporous polymers | Structure |
|---|---|
| PIM-1 | 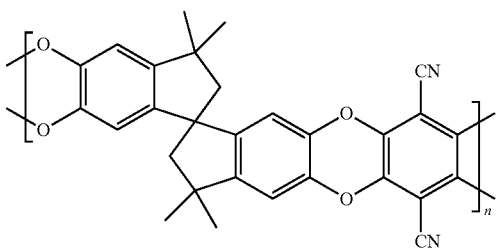 |
| PIM-7 | 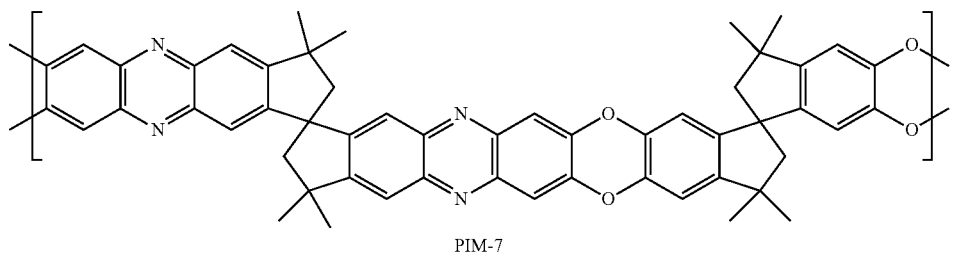 |

PIM-7

-continued
| Rigid microporous polymers | Structure |
|---|---|
| PIM-8 | 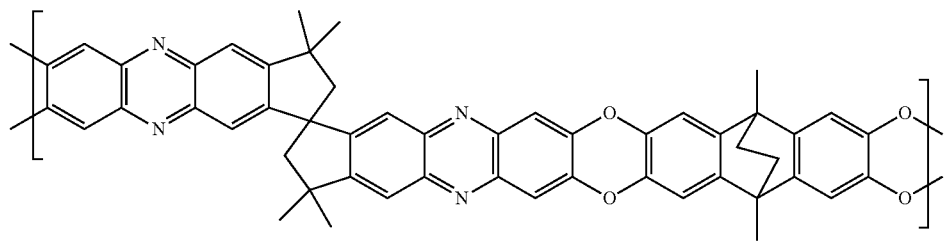<br>PIM-8 |
| PIM-9 | 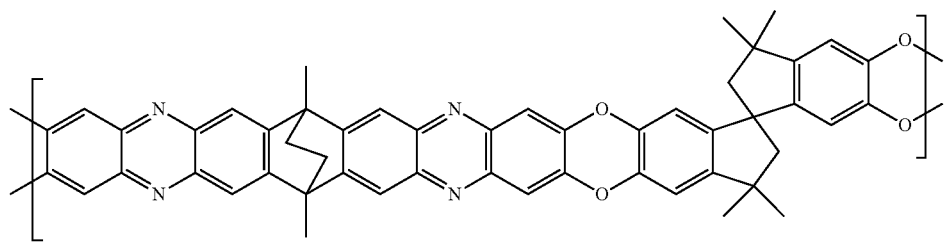<br>PIM-9 |
| KAUST-PI-1 | 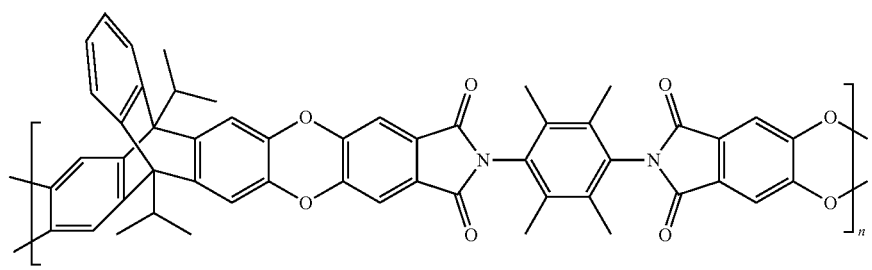<br>KAUST-PI-1 |
| PIM-BADAS-1 | 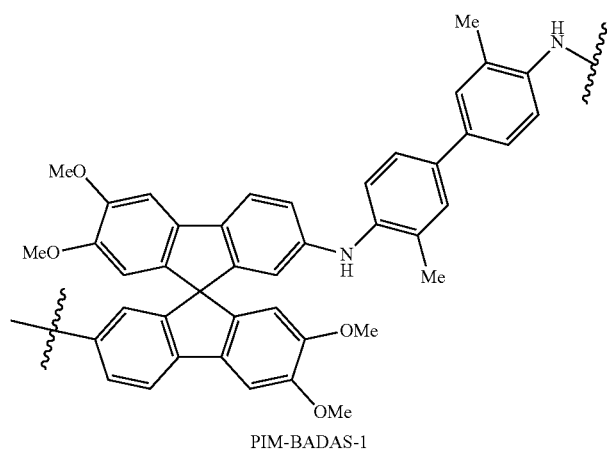 [SMILES: *Nc1ccc(-c2ccc(Nc3ccc4c(c3)C3(c5cc(*)ccc5-c5cc(OC)c(OC)cc53)c3cc(OC)c(OC)cc3-4)c(C)c2)cc1C]<br>PIM-BADAS-1 |

-continued

| Rigid microporous polymers | Structure |
|---|---|
| PIM-DUCKY-1 | 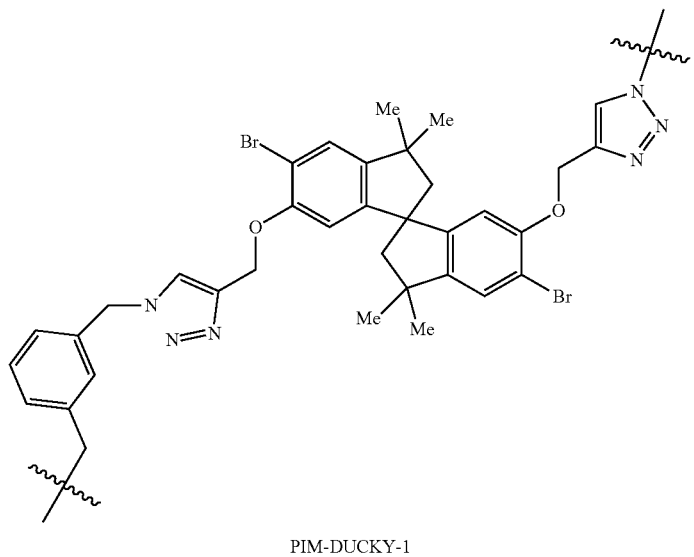 [SMILES: *Cc1cccc(CN/C=C(/COc2cc3c(cc2Br)C(C)(C)CC32CC(C)(C)c3cc(Br)c(OCc4cn(*)nn4)cc32)N=N)c1] PIM-DUCKY-1 |
| PIM-Tz$_{25}$ | 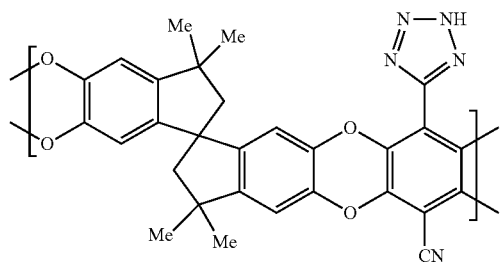 PIM-Tz$_{25}$ (25% tetrazole) |
| PIM-DUCKY-2 | 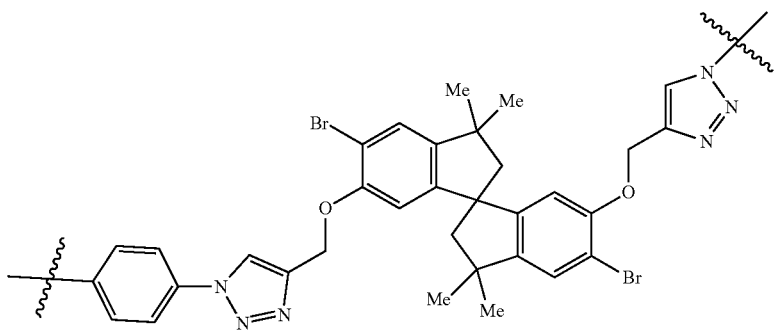 PIM-DUCKY-2 |

Selection of the polymeric material for use in preparing a powder or film to be pyrolyzed to form sieve particles may be made based on the heat resistance, chemical resistance, mechanical strength, and tailored separation properties, as well as other factors dictated by the operating conditions for selective permeation. In some embodiments, the carbon molecular sieves are prepared from the pyrolysis of aromatic polyimides or cellulosic polymers. The pyrolysis of suitable precursors, generally under conditions conventionally used to produce carbon sieves, can result in a product that has a certain microporosity of molecular dimensions which is responsible for the molecular sieve properties of the carbons.

During the pyrolysis process, the heating can be affected under a reactive gas atmosphere. Controlled thermal degradation of the polymer precursor results in a pore opening, and thus predetermined pore-size ranges can be obtained, suitable for the intended separation process.

The molecular sieve membrane described herein is a carbon-based molecular sieve membrane. However, in some embodiments, the carbon molecular sieve can be an adsorbent, catalyst, composite, or a filter. The sieves described herein can be prepared by pyrolyzing the polymeric precursor in accordance with the above-mentioned processes. For example, the molecular sieve can be prepared by pyrolyzing a polymeric film or other continuous polymeric body. In some embodiments, one can obtain fluid separation membranes having pore size and a pore size distribution that effectively separate specific mixtures of gases, fluids, etc. In some embodiments, the carbon molecular sieve can include ultra-micropores from 5 Å to 20 Å (e.g. 7 Å, 9 Å, 11 Å, 13 Å, 15 Å, 18 Å), which is a range that can work for xylene isomer separations. Moreover, the carbon molecular sieve can include a $sp^3/sp^2$ hybridized carbon ratio in the sieve from 0.10 to 1.0 (e.g. 0.20, 0.40, 0.60, 0.70, 0.80, 0.90). In some embodiments, the carbon molecular sieve membranes can have a surface area from 2 $m^2/g$ to 1000 $m^2/g$ (e.g. 14 $m^2/g$, 447 $m^2/g$, 450 $m^2/g$, 461 $m^2/g$, 471 $m^2/g$). In some embodiments, the carbon molecular sieves have a p-xylene permeability from 1 to 1000 times larger than a p-xylene permeability of a membrane prepared without $H_2$ during the heating (e.g. 5 times, 10 times, 14 times, 20 times, 100 times, 250 times, 500 times, 750 times). In some embodiments, the carbon molecular sieve membranes have a p-xylene permeability from $$8.5 \times 10^{-18} \frac{\text{mol} \times m}{m^2 \times s \times \text{Pa}} \text{ to } 8.5 \times 10^{-8} \frac{\text{mol} \times m}{m^2 \times s \times \text{Pa}}.$$

$$\left(\text{e.g. } 8.5 \times 10^{-16} \frac{\text{mol} \times m}{m^2 \times s \times \text{Pa}} \text{ to } 8.5 \times 10^{-10} \frac{\text{mol} \times m}{m^2 \times s \times \text{Pa}}, \right.$$

$$\left. 8.5 \times 10^{-15} \frac{\text{mol} \times m}{m^2 \times s \times \text{Pa}} \text{ to } 8.5 \times 10^{-13} \frac{\text{mol} \times m}{m^2 \times s \times \text{Pa}} \right).$$

In other embodiments, a plurality of carbon molecular sieve can be combined in any suitable way to produce separations modules. These modules can be used as adsorbent beds or membrane beds. In some embodiments, the adsorbent beds and the membrane beds are used for gas and vapor separations, aqueous separations, organic separations, and hydrocarbon separations. Further contemplated is a process for performing a separation on a feed stream that can include a module. The feed stream can include a first component and a second component capable of forming a permeate stream enriched in the first component and a retentate stream depleted in the first component or enriched in the second component. In some embodiments, the feed stream can include a first component in a concentration range of 1 wt. % to 99 wt. % (e.g. 5 wt. % to 75 wt. %, 10 wt. % to 60 wt. %, 20 wt. % to 45 wt. %). In some embodiments, the feed stream is a natural gas stream. In sill some embodiments, the permeate stream that is enriched in first component that can include at least one of $CO_2$, $H_2S$, $H_2O$, He, and the retentate stream is enriched in second component that can include at least one of $CH_4$ and $N_2$. In other embodiments, the feed stream can include a $C_8$ aromatics stream, the permeate stream is enriched in first component that can include at least one of benzene, p-xylene, and the retentate stream that is enriched in second component that can include at least one of ethyl benzene, o-xylene and m-xylene. In some embodiments, the feed stream can include a virgin naphtha stream (IBP-380° F.), the permeate stream that is enriched in first component that can include at least one of n-paraffins and aromatics, and the retentate stream that is enriched in second component that can include at least one of iso-paraffins and cyclo-paraffins. In other embodiments, the feed stream can include a whole crude stream, the permeate stream that is enriched in first component that can include at least one of naphtha (IBP-380° F.) and kerosene fractions (380-530° F.), and the retentate stream that is enriched in second component that can include at least one of the remaining fraction (530° F.+). In some embodiments, the feed stream can include a heavy hydrocarbon stream such as bitumen, atmospheric resid, vacuum resid, steam cracker tar, fluid catalytic cracker main column bottom, the permeate stream that is enriched in first component that can include at least one of saturates and/or 3– ring aromatics, and the retentate stream that is enriched in second component that can include at least one of 3+ ring aromatics, asphaltenes, metals, and/or micro-carbon residue.

The favorable combination of micro porosity, rigidity, thermal, chemical and mechanical stability imparted by the reactive pyrolysis process allows for high permeability and selectivity of these membranes for both gas and liquid separations. The membranes based on the polymer precursor separate the molecules based on the relative difference between their solubility and diffusion (molecular size and shape) through the ultra-micropores and micropores.

The membranes have a molecular weight cut-off (i.e., >90% rejection of species higher than a specified molecular weight) in the 150-2000 Dalton range (e.g., 150-1500 Dalton range, 150-600 Dalton range). The pore size of the membranes can be in the range of 5-20 Å making them suitable for the separation of a range of gas and liquids in petrochemical, refining, upstream, natural gas, air purification and pharmaceutical applications.

The membrane can achieve size-based separation of whole crude and crude fractions. Typical whole crude molecular weight ranges from 50-2000 Dalton. The membranes can provide a naphtha or kerosene cut out of the whole crude where the membrane has a MWCO of 100-500 Daltons. Within the naphtha and kerosene range the membranes can separate further based on MW and molecular class. These membranes can be exploited to give class-based separation of aromatics, cyclo-paraffins, n- and iso-paraffins within a certain crude fraction such as the naphtha (IBP-380° F.) and kerosene (380-530° F.), distillate (530-650° F.) and vacuum gas oil (650-1050° F.) fractions. Due to the MWCO of these membranes in the <500 Dalton range, the membranes can be used to remove asphaltenes, multi-ring (3+ ring) aromatics, hetero atoms, metals (Nickel, Vanadium, Iron, Calcium), sulfides from crude oil and its fractions.

The membranes can further be utilized in a nanofiltration mode for the removal of homogenous catalysts such as Rhodium, Nickel Ligand based, cobalt carbonyl catalyst from organic solvents, polyolefin oligomer and polymers from hexane, sulfolane/NMP solvents from vacuum resid or vacuum gas oil range aromatic molecules, metallocene catalyst in higher olefins from solvents and lube oil from solvents such as MEK and toluene. The membranes can be utilized for the dehydration of organics such as alcohols (ethanol, butanol) or ketones from water. Carbon-molecular sieve membranes provide the required structural, chemical, and mechanical stability to the membranes which enables the separation of various organic molecules which would otherwise swell, plasticize or dissolve polymeric membranes significantly reducing their practical lifetime.

The CMS can alternatively be used in reactive separations due to their high thermal, chemical and mechanical stability. Membrane reactors enable selective permeation of a product or reactant molecule thus improving the efficiency of equilibrium-controlled reactions. Examples of membrane reactors include p-xylene selective membrane to improve the efficiency of vapor or liquid phase isomerization reaction, $H_2$ selective membrane to improve the efficiency of direct methane to liquids reaction, water gas shift conversion reaction and propane dehydrogenation reaction, improving esterification yields by removal of water.

The membranes can be used in processes with multiple stages or a cascade type configuration operating under various modalities, e.g. nanofiltration (NF), reverse osmosis (RO), forward osmosis (FO), pressure retarded osmosis (PRO), pervaporation, gas separations, vapor separations and with different geometries, e.g. hollow fiber, monolith, spiral wound, and plate-frame, disc, coupons. The membrane process can be operated to get a permeate yield from about 1 wt. %-99 wt. %. Flux through the membrane can vary depending on the membrane pore size and test conditions. The flux to be in the range of about 0.1-20 gallons/ft2/day range.

Membranes employed in this process should be stable at temperature from about 75-932° F. (24-500° C.) (e.g., 120-775° F. (49-413° C.), 212-525° F. (100-274° C.), 361-454° F. (183-234° C.). Membranes used herein should be able to withstand transmembrane pressures greater than from about ambient to about 2000 psig (about 13.8 MPag) depending on the membrane modality. For NF and RO the feed is pressurized typically from about 100 psig (about 700 kPag) to 2000 psig (about 13.8 MPag), with about 2000 psig (about 13.8 MPag) being a typical limit for a commercial membrane module. In NF and RO the permeate side is typically from ambient pressure to about 100 psig (about 700 kPag). In pervaporation the feed is anywhere from ambient to about 60 psig (about 400 kPag) and the permeate side is at a vacuum with pressures being typically about 0.2-0.3 bar (3-5 psia) but can be as low as about 0.02 bar. In FO pressure differential does not drive the separation but rather, the driving force is forward osmotic pressure by use of a concentration gradient. In FO a large molecule naturally draws the faster permeating species through the membrane because of its higher osmotic pressure. FO requires another separation step in the permeate but the draw molecule is quite large in comparison to the permeate molecule and then can be easily separated using known techniques, such as distillation.

The membranes may be positioned in a single membrane unit (stage) or in several units, wherein each unit may be comprised of one or more separate membranes. Typically, the number of membrane units may depend on the surface area of the separate membranes in combination with the required quantity of steam to be permeated. The membrane units may include membranes of the same type, or a different type, in terms of composition or configuration. As a consequence, the membrane units may differ from each other, in terms of one or more of shape, permeance, permselectivity, or surface area available for permeation. Furthermore, the membranes may be arranged in series or in parallel, for example.

The carbon molecular sieve (CMS) membranes of the present invention are believed to be ultra- and microporous materials that have distributions of pore sizes and interconnected channels that enable enhanced permeation of molecules. Within the distribution of pore sizes are constricted, ultramicroporous pore openings with dimensions that are of the same order of magnitude as molecular sizes of molecules. It is generally believed that "ultramicropores" perform the molecular sieving (size-selective) process in carbon molecular sieve materials, while larger "micropores" connecting ultramicropores provide sorption cavities and allow for high fluxes of gas penetrants by promoting larger average diffusional jumps. Thus, the porous nature of carbon molecular sieves of the present invention provides their capability for high gas permeabilities, yet their molecular sieving morphology permits precise discrimination of gas penetrants to yield highly selective membranes. Moreover, in a typical pyrolysis the ultra-micropore collapses, but a in a pyrolysis in accordance with the disclosed exemplary embodiments, the ultra-micropore does not collapse.

PIM-1 polymer used in the pyrolysis process can be obtained as follows. Its synthesis can begin with a reaction of tetrafluoroterephthalonitrile (TFTPN) and 5,5',6,6'-tetrahydroxy-3,3,3',3'-tetramethyl-1,1'-spirobisindane (TTSBI) in dimethylformamide solvent. Using a PIM-1/tetrahydrofuran solution casting method, a fluorescent yellow, free-standing dense polymeric PIM-1 films can be prepared.

Figure 2A:
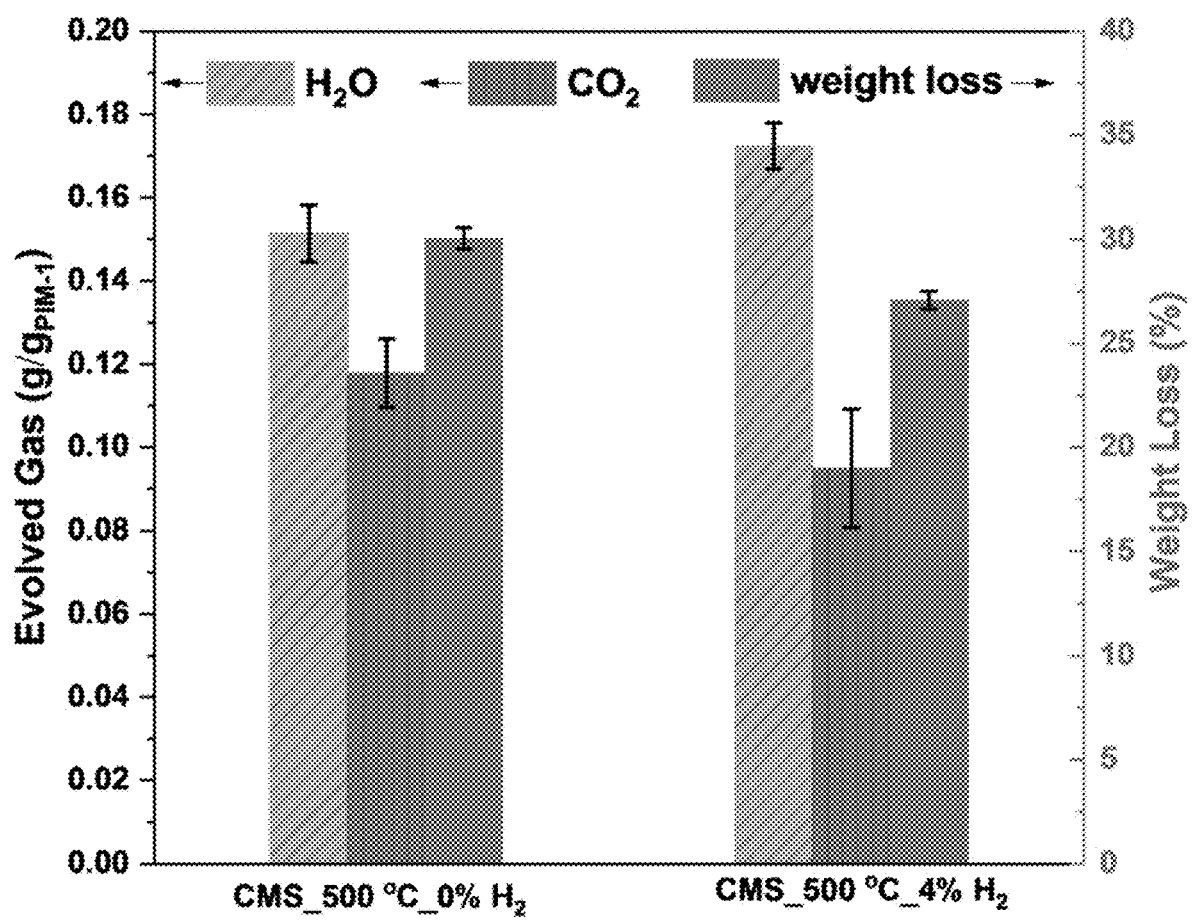
FIGS. 2A-2C depict the influence of hydrogen included pyrolysis on the CMS formation process in accordance with an exemplary embodiment of this disclosure.
Figure 2B:
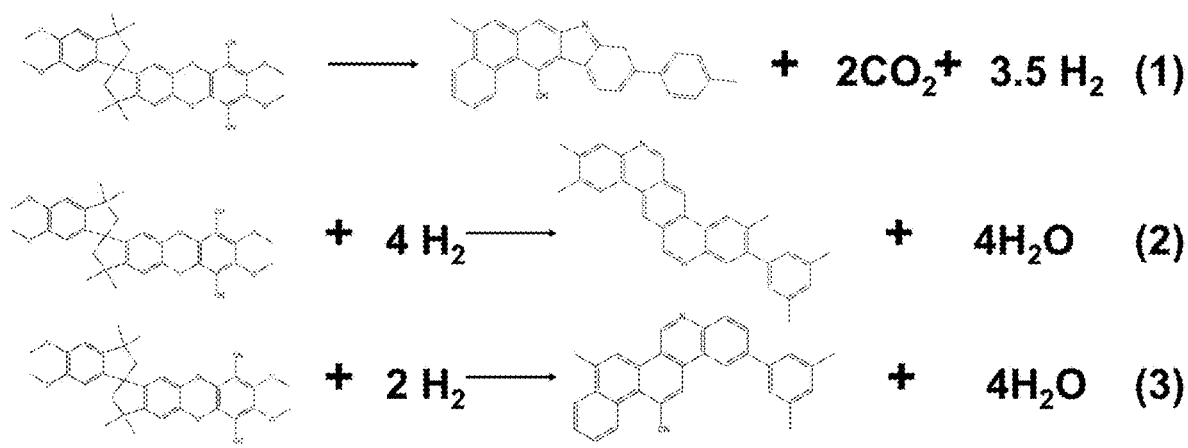
Figure 2C:
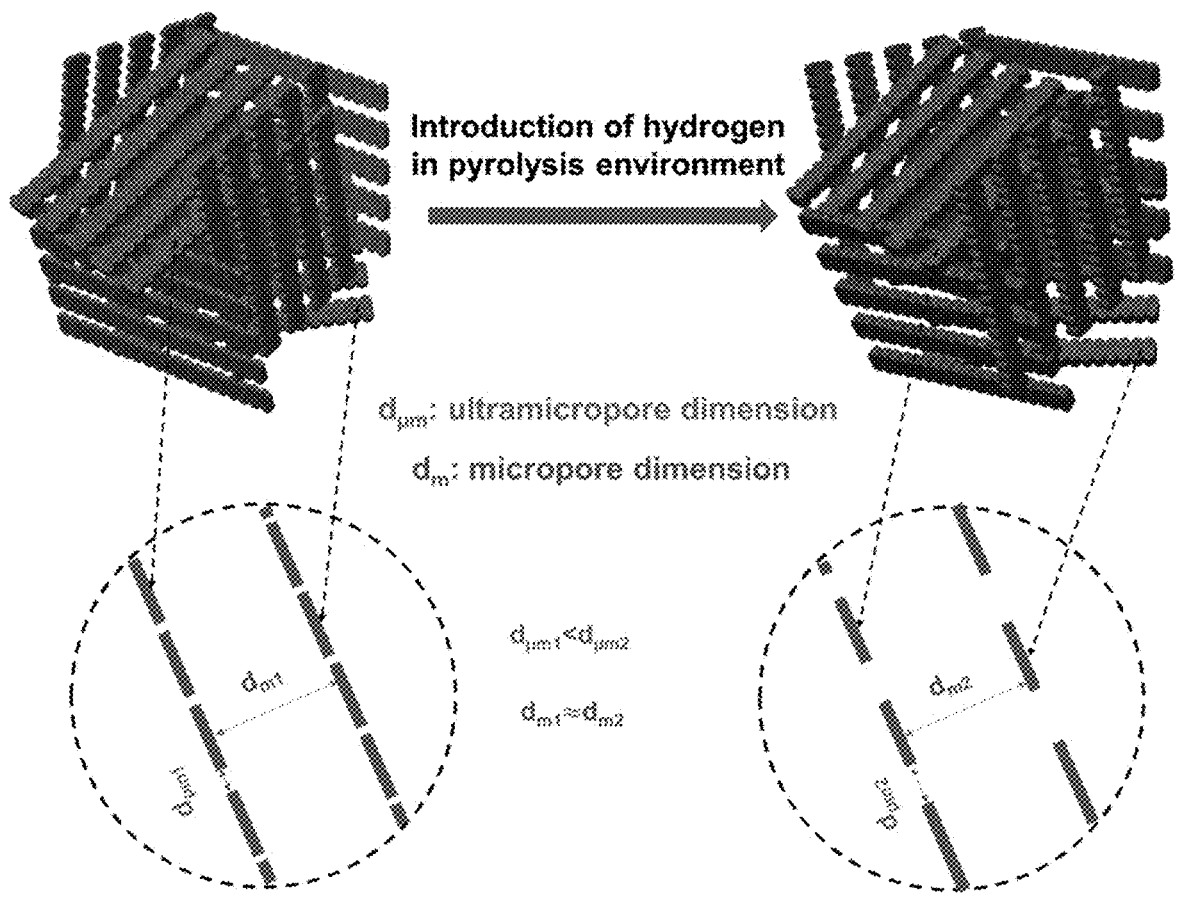

The carbon molecular sieve material can be amorphous, isotropic and/or microporous. Initially, in the thermal ramp process, the entangled semi-flexible PIM-1 precursor undergoes aromatization and fragmentation and can experience sufficient localized stresses, which cause periodic scissions along its backbone. Such backbone scissions occur with $CO_2$ and $H_2O$ generated to remove most of the oxygen atoms of PIM-1, resulting in possible rigid, highly aromatic strands. Based on the amount of evolved $CO_2$ and $H_2O$ (measurable by mass spectroscopy), as shown in FIG. 2A, hypothetical reaction pathways are proposed in FIG. 2B. The generated reaction products then connect with each other to form rigid strands. The rigid strands can then organize into more packable plates to have an overall higher entropy value and reduce the exclude volume present within a "random" phase packing of strands. It should be noticed that the lateral linkages between strands can occur for reactive consolidation purposes, evolving molecular $H_2$ in the process. However, kinetic restrictions (e.g. limited time for final "ramp" and "soak" periods with high temperature) lead to the imperfect organization of strands within the plates themselves and long-range plates stacking defects. A typical idealized micropore "cell" was formed with imperfectly packed plates comprising imperfectly organized strands. In CMS materials, the slits between strands are ultramicropores enabling molecular sieving while the voids between plates are micropores providing abundant sorption sites. During the soak and cooling phases, ongoing formation and coalescence (sharing ultramicropores "walls" between cells) of multiple neighboring cells will generate an idealized CMS structure with a bimodal distribution of pores. In some embodiments, cool down rate of the process is from 0.1° C./min to 200° C./min (e.g. 10° C./min, 25° C./min, 50° C./min, 75° C./min, 100° C./min, 125° C./min, 150° C./min, 175° C./min). The enlargement of ultramicropores due to the introduction of $H_2$ is illustrated in FIG. 2C and can be explained in two ways. On the one hand, the existence of $H_2$ in the pyrolysis environment will inhibit the loss of oxygen in the form of $CO_2$ and promote the remove of oxygen atoms in the form of $H_2O$, which is proved by FIG. 2A. As a result, the formed strands in the $H_2$ included pyrolysis environment will be more kinked comparing with those formed in pure Ar. This kinked structural nature will make the alignment of strands much more difficult, which increase the imperfection of strands and therefore the size of the ultramicropores. On the other hand, considering Le Chatelier's principle, the consolidation of lateral stands would be suppressed by $H_2$ molecules presenting in the atmosphere resulting in larger slits between strands. Because of these two contributors, the size of ultramicropores inside the $H_2$ assisted CMS is significantly increased, and thus, the $H_2$ can inhibits the pore structure collapse during pyrolytic formation of CMS. The ultra-selective separation performance of the CMS can be attributed to the unique "slit-like" bimodal pore structure of CMS.

EXAMPLES

The following examples are illustrative, but not limiting, of the methods and compositions of the present disclosure. Other suitable modifications and adaptations of the variety of conditions and parameters normally encountered in the field, and which are obvious to those skilled in the art, are within the spirit and scope of the disclosure.

Example 1: Synthesis of PIM-1

PIM-1 was synthesized using a low-temperature polycondensation method. The two purified monomers, tetrafluoroterephthalonitrile (TFTPN) and 5,5',6,6'-tetrahydroxy-3,3,3',3'-tetramethyl-1,1'-spirobisindane (TTSBI), were added into anhydrous dimethylformamide (DMF) with an equimolar ratio in a round-bottom flask. After the monomers were completely dissolved, anhydrous highly crushed $K_2CO_3$ (2.5 times with respect to TFTPN monomer molar concentration) was added to the solution, and the polymerization reaction was continuously stirred under a nitrogen atmosphere at 65° C. for 72 hrs. After the reaction, upon cooling, deionized water was used to quench the reaction and precipitate the PIM-1 polymer. The crude product was then collected by filtration and washed with additional deionized water to remove salts and solvent residues. Repeated reprecipitation from chloroform further purified the polymer. Finally, the fluorescent yellow PIM-1 polymer was dried in vacuum oven under 70° C. for 12 hrs before use. The molecular weight as determined by gel permeation chromatography (GPC) in tetrahydrofuran (THF) was $M_n$=46,500 with a PDI=1.5 when compared against polystyrene standards.

Example 2: Polymeric Film Preparation

The dried PIM-1 (0.5 g) was dissolved in THF (25 g) to form a 2 wt % polymer solution and placed on a roller at room temperature for 6 hrs to form a homogeneous solution. The resulting polymer solution was then used to prepare polymeric PIM-1 films by a solution casting method inside a glove bag (Glas-Col) in a fume hood at room temperature. The polymer solution, a glass plate, a doctor blade, a beaker containing excess THF were placed inside the glove bag prior to casting process. The glove bag was then sealed, purged with nitrogen three times, and fully saturated with THF for 5 hrs. Afterwards, the solution was transferred from the vial to the glass plate and cast into a uniform film. Subsequently, the film will solidify as the THF slowly evaporates in the glove bag for 3 days, followed by vacuum drying for another 24 hrs before use.

Example 3: PIM-1-Derived CMS Membranes Fabrication

CMS membranes were fabricated from polymeric precursor (PIM-1) films in a pyrolysis set-up located inside a fume hood as described in FIG. 1. Dried circular PIM-1 polymeric films were first placed on a stainless steel mesh plate, put into a quartz tube and loaded into a three zones pyrolysis furnace (OTF-1200X-III-S-UL, MTI Corporation). With three thermocouples independently connected to the three channels of the controller, the temperature distribution inside the quartz tube was uniform. Sealing of the quartz tube was insured by a pair of SS 304 vacuum flanges with double high-temperature silicone o-rings. An oxygen-free atmosphere was achieved by purging the tube with 4 vol. % hydrogen/argon mixed gas and/or UHP argon for at least 12 hrs. Two digital flow meters (Bubble-O-Meter) were used to monitor the flow rates of hydrogen/argon mixed gas and pure argon lines, which can precisely control the hydrogen concentration (0 to 4 vol. %) in the inert environment. A surface-mount hydrogen detector will be triggered if the hydrogen amount is higher than 8000 μm inside the fume hood given safety concerns. The typical oxygen concentration was below 0.5 ppm as measured by an oxygen analyzer (R1100-ZF Rapidox 1100ZF, CEA Instruments, Inc.). The heating protocols used were illustrated in Table 1 below.

TABLE 1

Heating protocols used to fabricate PIM-1-derived CMS

| Protocol phase | Step | Heating rate (° C./min) | Final pyrolysis temperature | | |
|---|---|---|---|---|---|
| | | | 500° C. | 800° C. | 1100° C. |
| Ramp | 1 | 10 | 25-200° C. | 25-500° C. | 25-800° C. |
| | 2 | 3 | 200-485° C. | 500-785° C. | 800-1085° C. |
| | 3 | 0.25 | 485-500° C. | 785-800° C. | 1085-1100° C. |
| Soak | 4 | 0 | Soak for 2 hrs at 500° C. | Soak for 2 hrs at 800° C. | Soak for 2 hrs at 1100° C. |
| Cool | 5 | — | Naturally cooling back to 25° C. under pyrolysis environment | | |

Example 4: Material Characterization by Nitrogen Physisorption

Figure 3A:
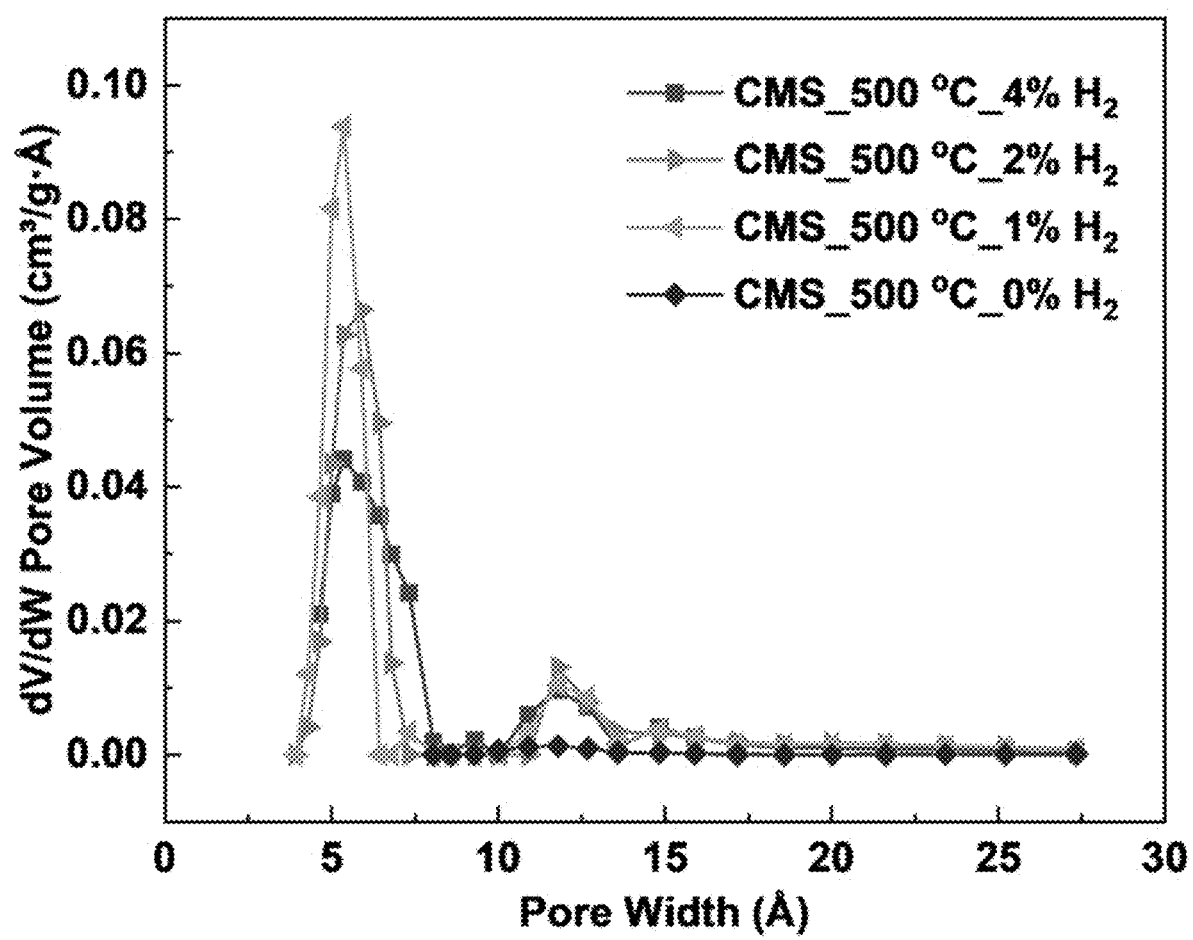
FIGS. 3A-3E depict characterization results for PIM-1 and CMS fabricated in accordance with various embodiments of this disclosure.
Figure 3B:
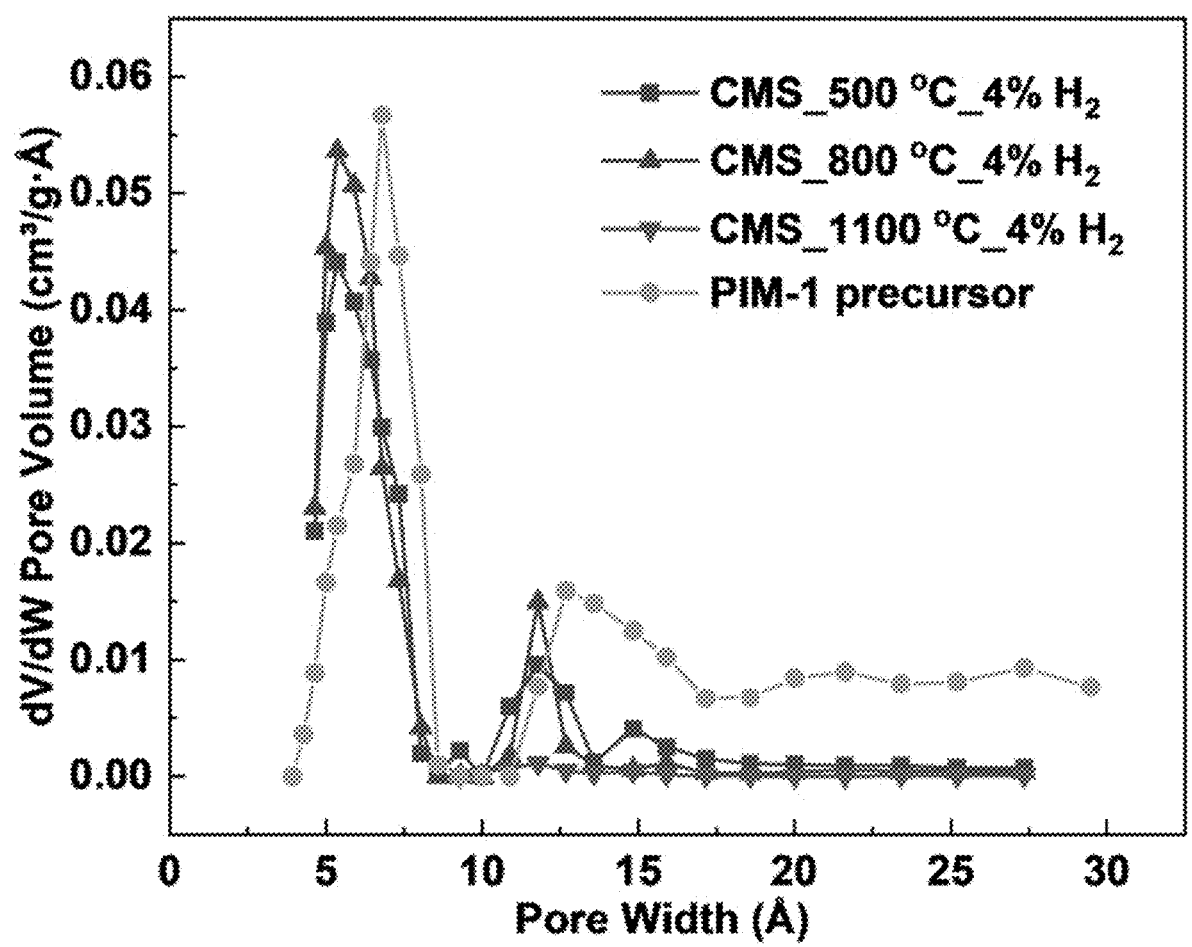

The tuning effect of $H_2$ on the pore structure of CMS is demonstrated in FIGS. 3A-3B. $N_2$ physisorption experiments are performed at 77 K. Four hydrogen volume fractions, 4 vol. %, 2 vol. %, 1 vol. % and 0 vol. % are chosen under the final pyrolysis temperature of 500° C. Reasonable $N_2$ physisorption isotherms at 77 K for CMS membranes pyrolyzed under 0% $H_2$ atmosphere could not be obtained, indicating that the size of ultramicropores inside these CMS is quite similar to $N_2$ (3.64 Å) and resulting in extremely slow $N_2$ diffusion. In contrast, the CMS pyrolyzed under $H_2$ included environment showed ultramicropores ranging from 5 to 20 Å. Moreover, the distributions of ultramicropores are narrower when the hydrogen amount decreases from 4 vol. % to 1 vol. %. The inhibition effect of $H_2$ on the structure collapse during pyrolysis process can also be understood in the way that the ultramicropores inside the PIM-1 precursor will be protected better with more $H_2$ existing. It can be observed that the distributions of micropores have little change for different $H_2$ amount conditions (e.g. 1 vol. %, 2 vol. %, 4 vol. %), as shown in FIG. 3A. Moreover, by comparing the pore size distribution of CMS samples pyrolyzed under 500° C. and 800° C., it can be seen that higher pyrolysis temperature can narrow both the micropores and ultramicropores. However, under very high pyrolysis temperatures (e.g. 1100° C.), severe structure collapse occurs under the existence of $H_2$. Accordingly, the above analysis indicates that both final pyrolysis temperature and $H_2$ concentration in the pyrolysis atmosphere each essentially affect the pore structure of CMS.

Nitrogen physisorption experiments were performed in Belsorp MAX (MicrotracBEL, Japan) at 77K. 2D-NLDFT (two-dimensional non-local density functional theory) pore size distribution calculations were obtained from $N_2$ isotherms by the BJH method with Micro Active software package (Micromeritics, USA). The total pore volume, as shown in Table 2 below, was calculated based on the total amount of $N_2$ adsorbed at $P/P_0$ of 0.95. The samples were degassed under vacuum on a Belsorp-Vac II below $10^{-2}$ kPa for 12 hrs at 110° C. The free space measurement was performed after each analysis.

TABLE 2

Pore volume from $N_2$ physisorption experiments for PIM-1 precursor and CMS materials under different conditions

| Sample | Pore volume (cm³/g) | Surface area (m²/g) |
|---|---|---|
| PIM-1 precursor | 0.725 | 723 |
| CMS_500° C._0% $H_2$ | 0.007 | 23 |
| CMS_500° C._1% $H_2$ | 0.153 | 450 |
| CMS_500° C._2% $H_2$ | 0.158 | 461 |
| CMS_500° C._4% $H_2$ | 0.161 | 471 |
| CMS_800° C._4% $H_2$ | 0.156 | 447 |
| CMS_1100° C._4% $H_2$ | 0.004 | 14 |

Example 5: Carbon Bonding Tests

In order to investigate the carbon bonding nature inside the samples, each spectrum from x-ray photoelectron spectroscopy for each of the CMS samples fabricated under different conditions is deconvoluted to three Gaussian peaks. X-ray photoelectron spectroscopy (XPS) was performed using a K-Alpha XPS (Thermo Fisher Scientific, West Palm Beach, Fla.), which is equipped with a monochromatic Al-K$\alpha$ X-ray source. Silver oxide was used as the internal standard to calibrate the spectra. The XPS analysis chamber was evacuated to a pressure of $2 \times 10^{-8}$ mbar or lower before collecting XPS spectra.

Figure 3C:
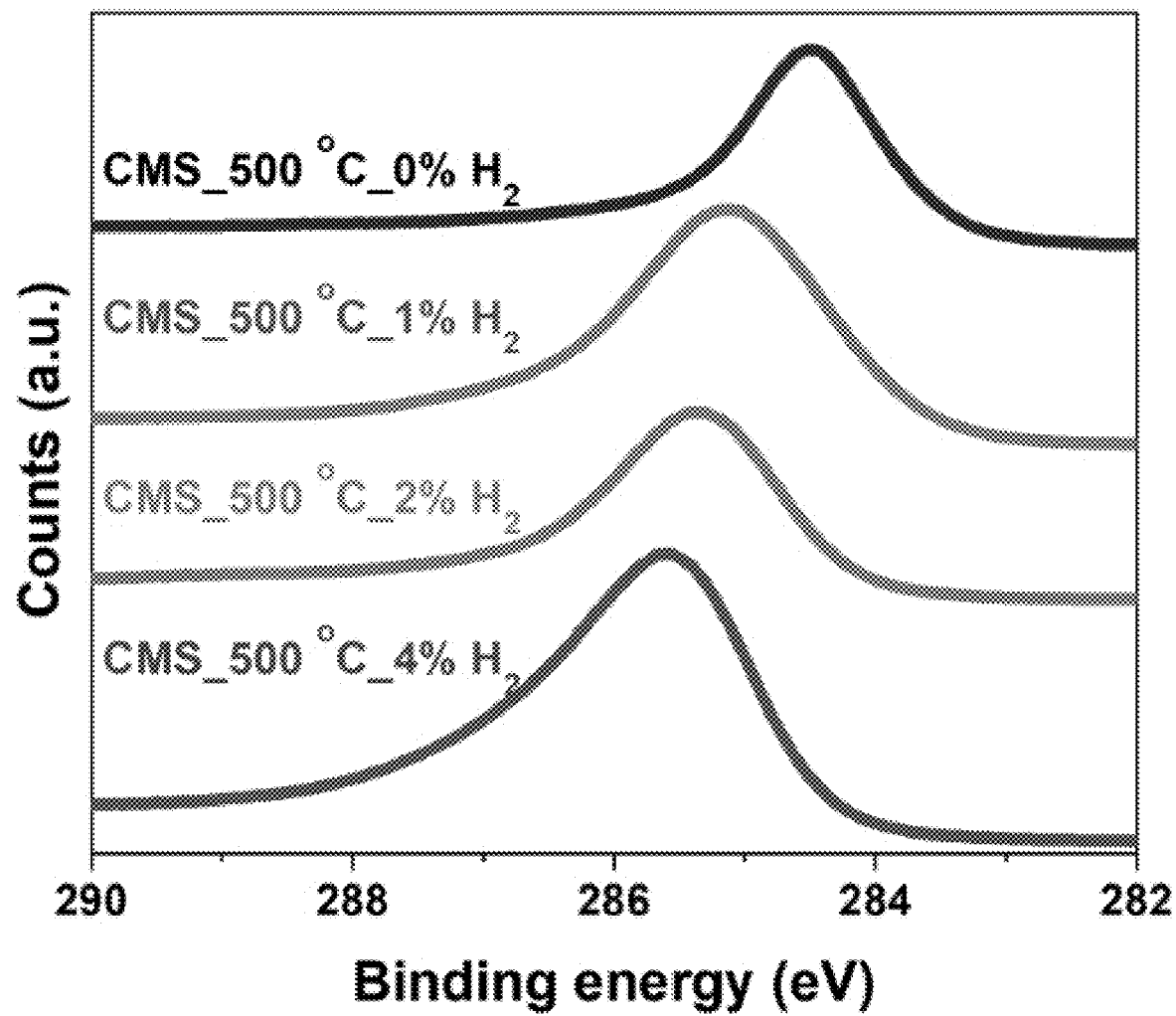
Figure 3D:
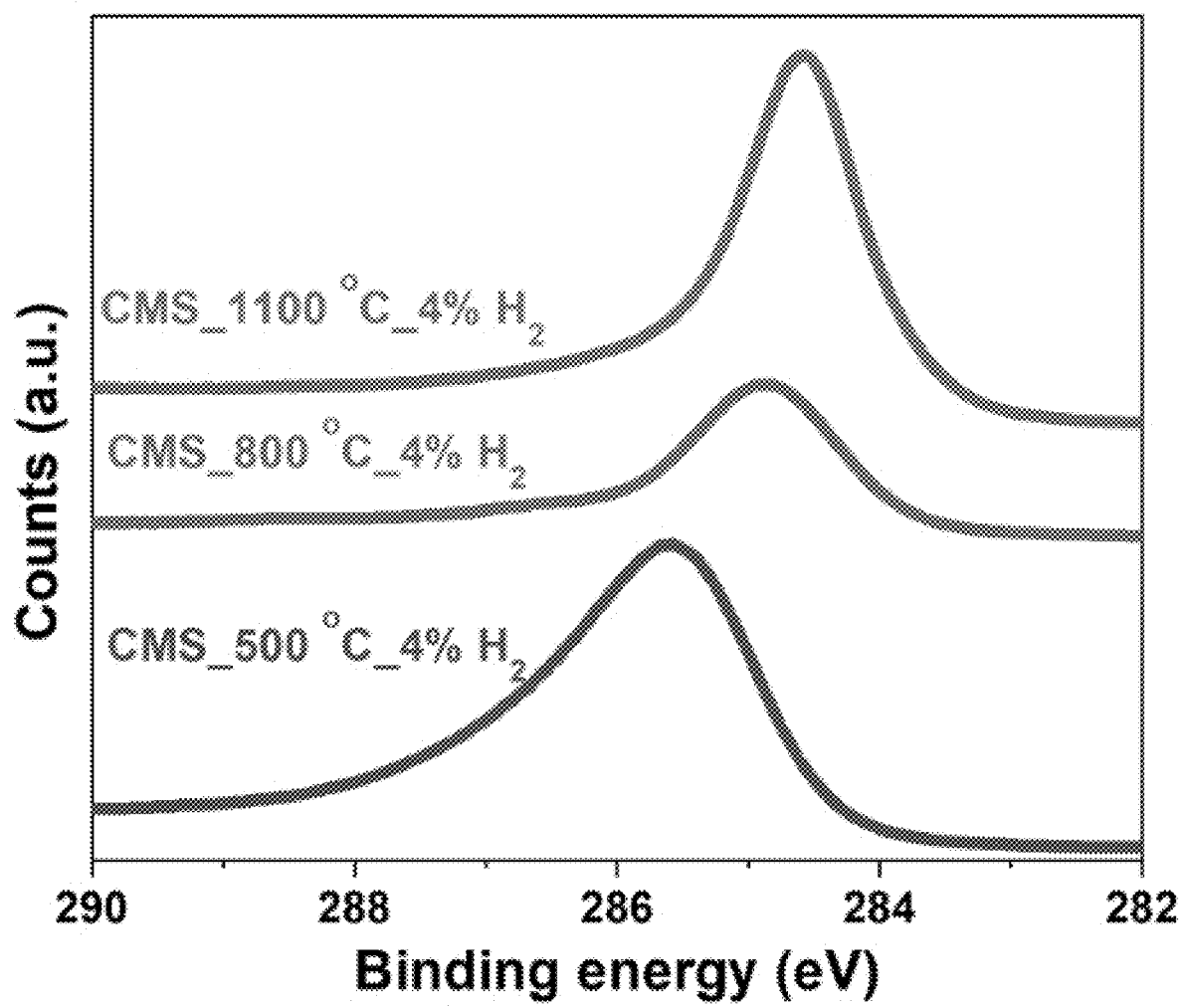
Figure 3E:
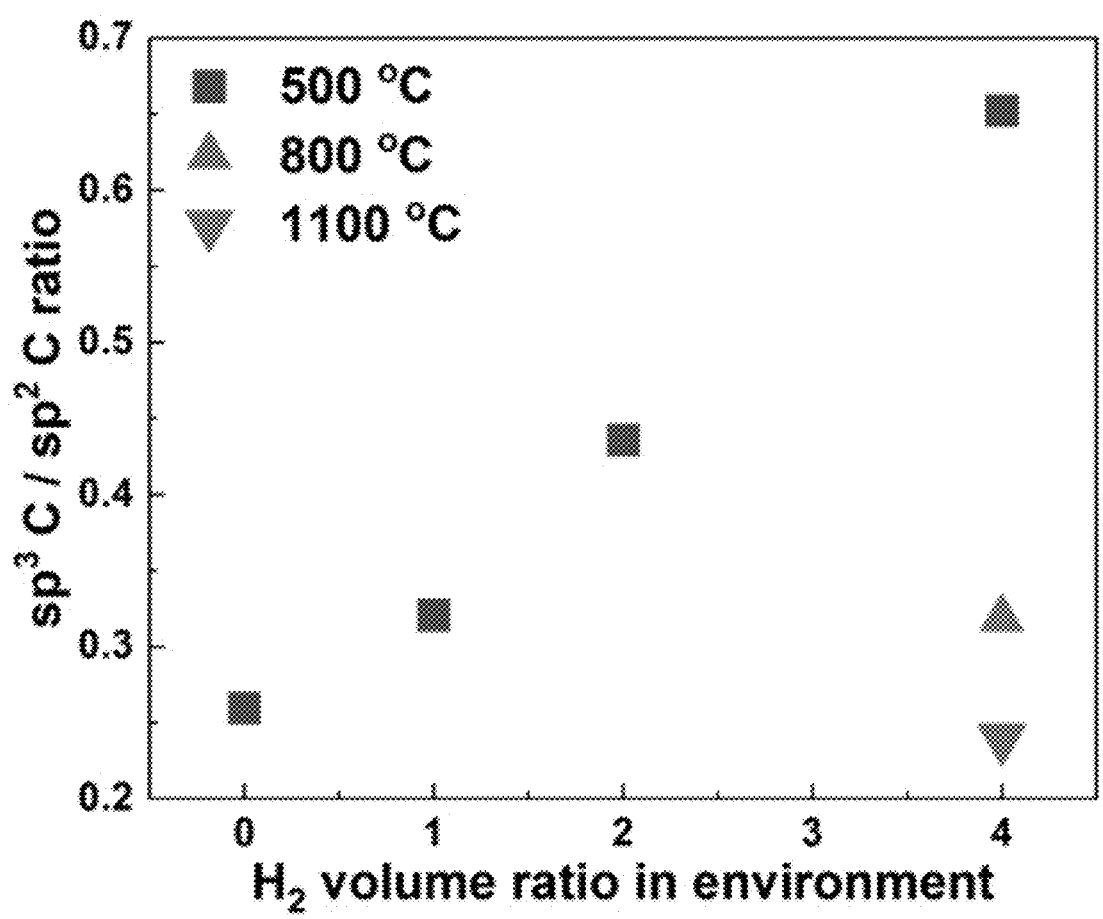

For all investigated samples, good fittings were obtained, indicated by a value of the square root of reduced $\chi^2$ of less than 3 and a coefficient of determination $R^2$ greater than 0.99. The two strongest signals with a relative binding energy distance of around 1 eV between their maxima are associated with different hybridization states. The signal at lower binding energy corresponds to the $sp^2$-hybridized carbon, a two-dimensional graphite layered structure, and the signal with an energy shift of around 1 eV is attributed to the $sp^3$ hybridized carbon. Moreover, a third signal observed around 289 eV is evidence of the existence of carbon state as C—O. The precise mechanism for the formation of the $sp^3$, a metastable state, is still not clear, but may be explained by the theory of collision cascade effects, which forms $sp^3$ carbon structure by carbon-carbon double bonds in close proximity by combining or "compressing". $Sp^3$ hybridized carbon, a three-dimensional structure, is useful for high flux while $sp^2$ hybridized carbon will lead to the collapse of the pore. The content of $sp^2$ and $sp^3$ hybridized carbon in each CMS sample can be estimated by their signal areas ratio. As shown in FIGS. 3C-3E, the $sp^3/sp^2$ carbon ratio in the CMS membranes increased monotonically with a decrease in pyrolysis temperature or an increase in hydrogen concentration. The increased $sp^3/sp^2$ carbon ratio also implies a higher free volume of the CMS samples.

Example 6: Organic Sorption Measurements

The gravimetric vapor sorption of single xylene component in PIM-1-derived CMS membrane was measured with a TA VTI-SA+ automated vapor sorption analyzer (TA Instruments, New Castle, Del.) at a relative pressure ranging from 0.000 to 0.400 at 55° C. Before each test, the carbon membrane was first crushed into smaller particles (average particle size is obtained from SEM) to enable sufficient sample loading and then dried in situ at 120° C. for 720 min under flowing nitrogen. The equilibrium criteria for each step was set for mass changes less than 0.0005 wt % over a 60 min period. Because of the instrument limitations, all uptake amounts at unit activity relative pressure point were measured manually for at least three times, each on fresh membrane. In each test, the PIM-1-derived CMS membrane was dried under vacuum at 120° C. for 12 hours to remove moisture and was weighed to obtain the initial mass value. After that, the membrane was soaked in pure p-xylene or o-xylene in a 20 mL vial and then placed in an oven at 55° C. for the measurements of pure component unit activity point. The samples were weighed after 25 and 30 days of soak and the sample weight was found to be identical in each case. Finally, the saturated membrane mass value was used to obtain the uptake amount at unit activity point.

Figure 4A:
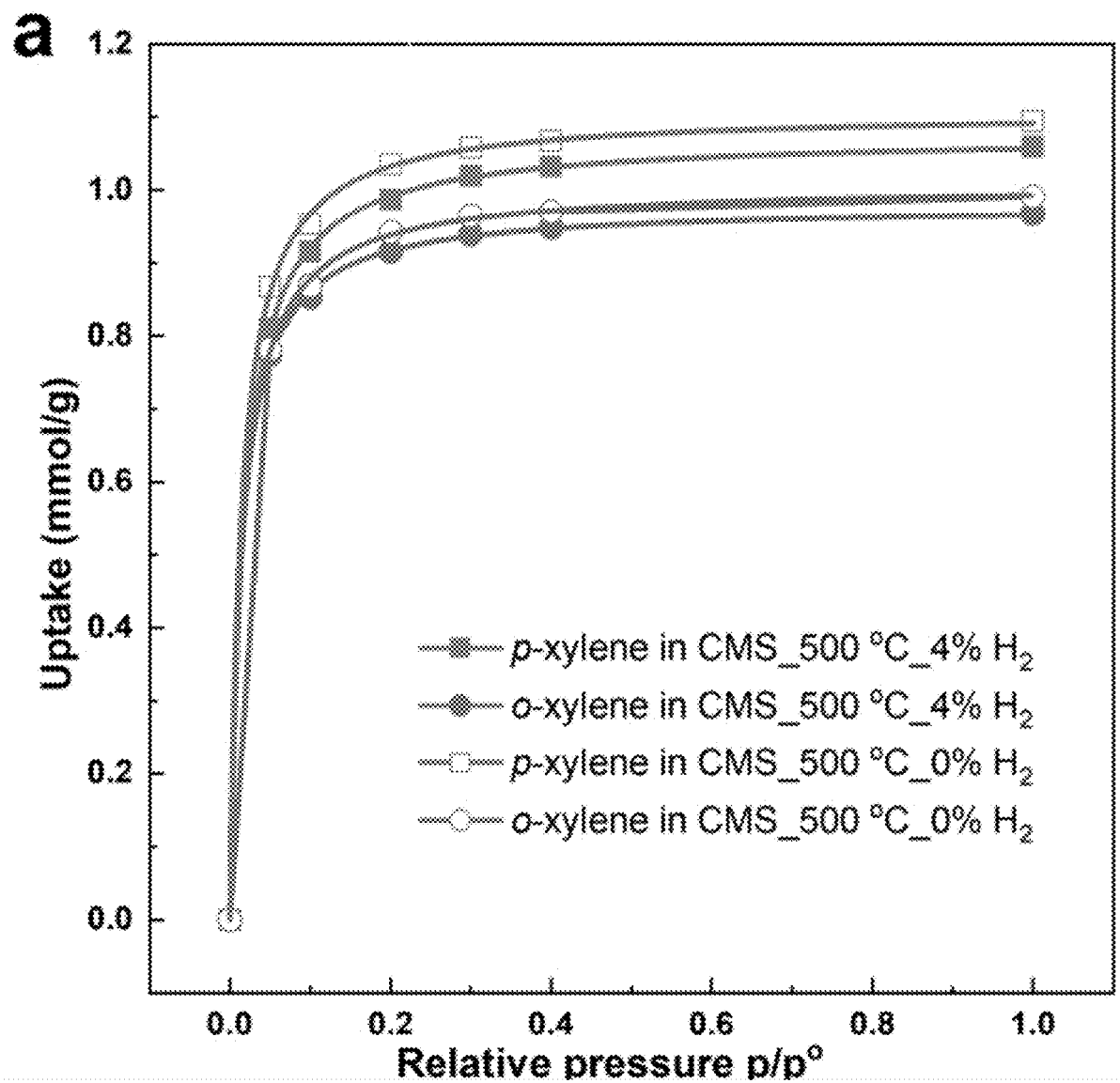
FIGS. 4A-4B depict adsorption and diffusivity performance of CMS membranes in accordance with an exemplary embodiment of this disclosure.
Figure 4B:
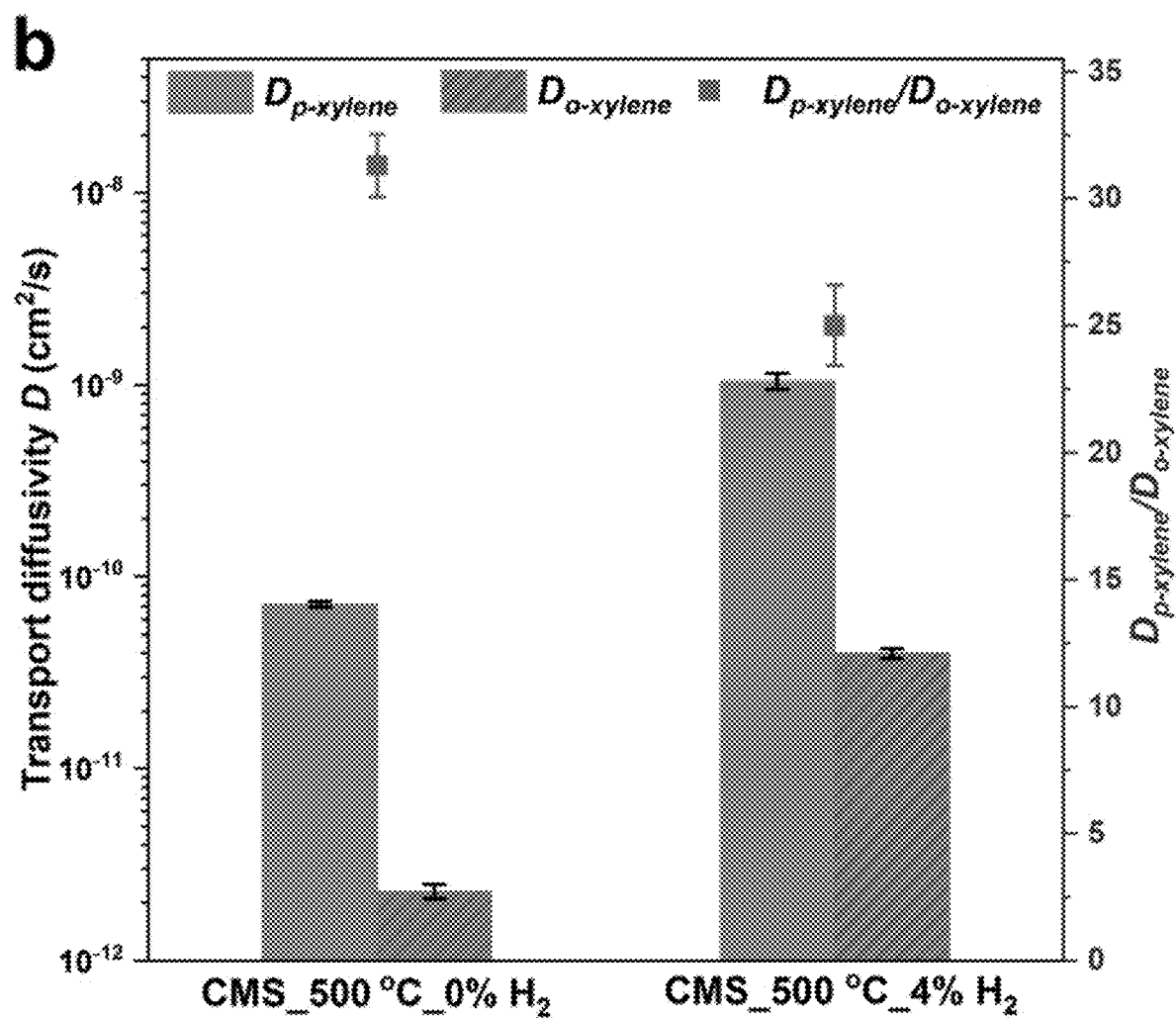

FIG. 4A shows the sorption isotherms of p-xylene and o-xylene collected at 55° C. for both CMS formed at 500° C. and 4% $H_2$ and CMS formed at 500° C. and 0% $H_2$. The uptake for p-xylene and o-xylene at each relative pressure exhibited only small differences (within 1 wt. %) relative to each other, revealing absence of a sorption-selective separation mechanism. However, surprisingly, the ultramicropores inside rigid CMS membranes enable molecular sieving and allow the faster diffusion of the smaller p-xylene molecule than the larger o-xylene molecule. As illustrated in FIG. 4B, after the introduction of $H_2$ in pyrolysis environment, the transport diffusivities increase significantly (at 55° C. and 0.05 relative saturation, $1.0 \times 10^{-9}$ cm²/s vs. $7.2 \times 10^{-11}$ cm²/s for p-xylene, $4.0 \times 10^{-11}$ cm²/s vs. $2.3 \times 10^{-12}$ cm²/s for o-xylene). This is mainly due to the less resistance to the diffusion of guest molecules provided by the rigid carbon structure with larger ultramicropores. Accordingly, $H_2$ assisted CMS exhibits a slightly lower diffusion selectivity, which indicates a trade-off between diffusion selectivity and diffusivity for CMS-type materials.

Example 7: Wicke-Kallenbach Permeation Measurements

The separation performance of the $H_2$ assisted PIM-1-derived CMS membranes can be tested by the Wicke-Kallenbach technique. For the Wicke-Kallenbach permeation measurements, the free-standing dense CMS membranes were fixed between rings of aluminum tapes (McMaster-carr Aluminum Masking Aluminum Tape, 0.003 inches thick) with outer diameter of 1 inch and inner diameter of ⅜ inch and sealed by a chemically-resistant epoxy (JB Weld MarineWeld).

The Wicke-Kallenbach permeation experiments for xylene vapors were conducted in the apparatus, which we used previously. Measurements were carried out until the equilibrium was reached, which was usually achieved after 24 h of continuous testing. The permeability of p-xylene or o-xylene measured via Wicke-Kallenbach permeation can be calculated by using Eq. 6.

$$\mathbb{P}_A = \frac{\dot{n}_A \times \ell}{A \times [p_{A,upstream} - p_{A,downstream}]} \quad (6)$$

$\dot{n}_A$ is the molar flow rate of p-xylene or o-xylene and can be obtained by a gas chromatograph and mass flow controller. Here, $P_{A,upstream}$ is set as $p_A^{sat}$, the saturated vapor pressure of p-xylene or o-xylene under relative operating temperature while $P_{A,downstream}$ is set as 0. $\ell$ is the thickness of the CMS membrane and is measured by SEM. A is the permeation area of the CMS membrane and can be obtained using Image J® software.

Figure 5A:
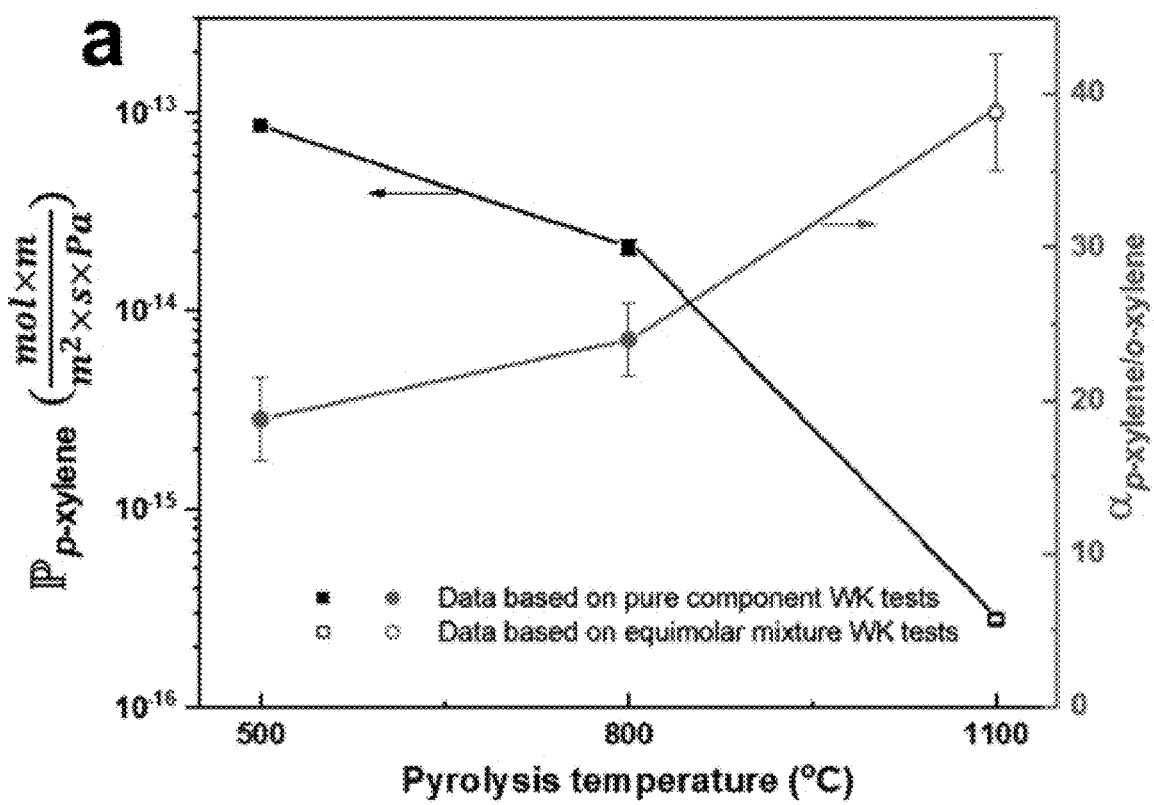
FIGS. 5A-5E depict permeation performance of CMS membranes in accordance with an exemplary embodiment of this disclosure.
Figure 5B:
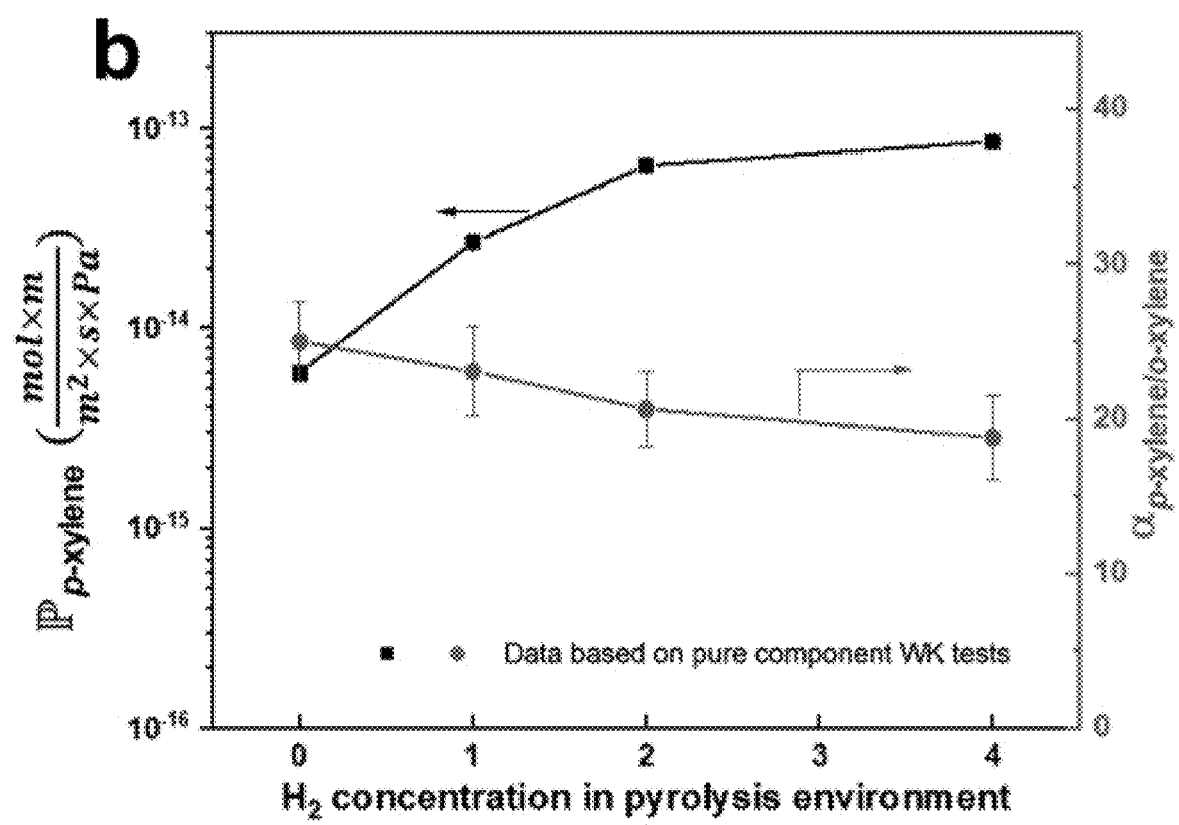
Figure 5C:
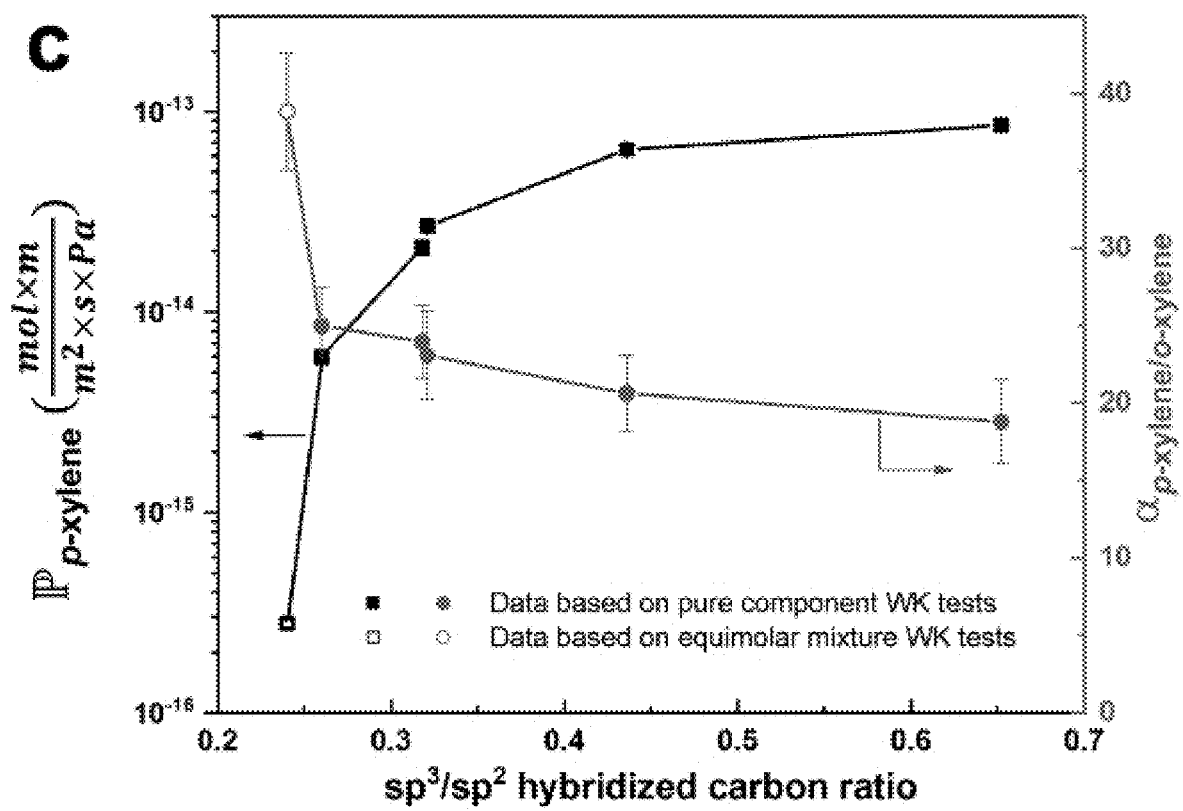

With the total pressure difference across the membrane maintained at zero, a feed of a pure xylene or xylene mixture flushes the upstream while nitrogen flows past the permeate side and then to a gas chromatograph to measure the xylene molecules that has permeated through the membrane. As illustrated in FIGS. 5A and 5B, lower pyrolysis temperature or higher $H_2$ concentration in the pyrolysis environment can result in higher permeability of p-xylene and lower permselectivity between p-xylene/o-xylene. It has been proved above that both the $H_2$ amount and pyrolysis temperature can effectively affect the pore size distribution and $sp^3/sp^2$ hybridized carbon ratio inside the CMS membranes. As mentioned previously, $sp^3$ hybridized carbon has a 3D structure contributing to the flux while $sp^2$ hybridized carbon mainly composes a planar structure incapacitated for permeability. This suggests a potential positive correlation between $sp^3/sp^2$ hybridized carbon ratio of the CMS membranes and permeability of guest molecules. As shown in FIG. 5C, as the $sp^3/sp^2$ hybridized carbon ratio increases from 0.24 to 0.65, the permeability of p-xylene through CMS membranes is indeed increased significantly from $2.8 \times 10^{-16}$ to $$8.5 \times 10^{-14} \frac{mol \times m}{m^2 \times s \times Pa} (\sim 30275\% \text{ increase})$$

while the permselectivity decreases slightly from 38.9 to 18.8 (~52% decrease).

Figure 5D:
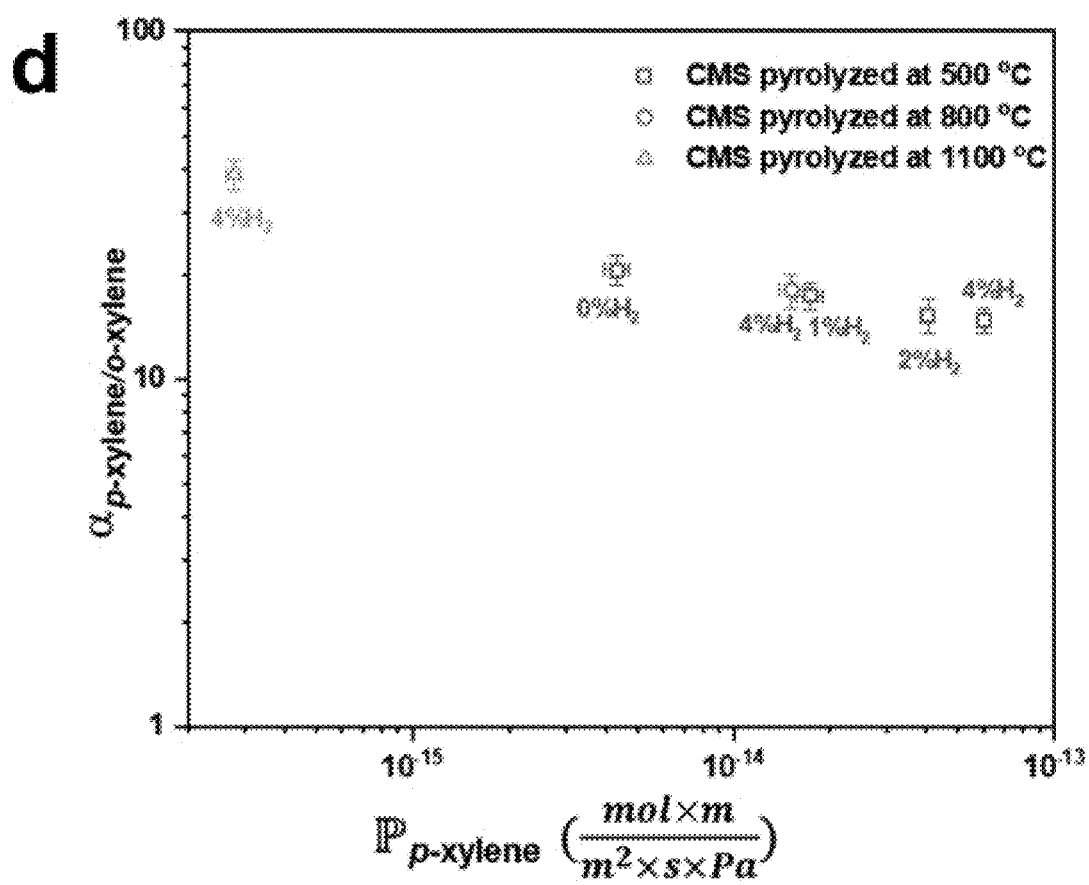
Figure 5E:
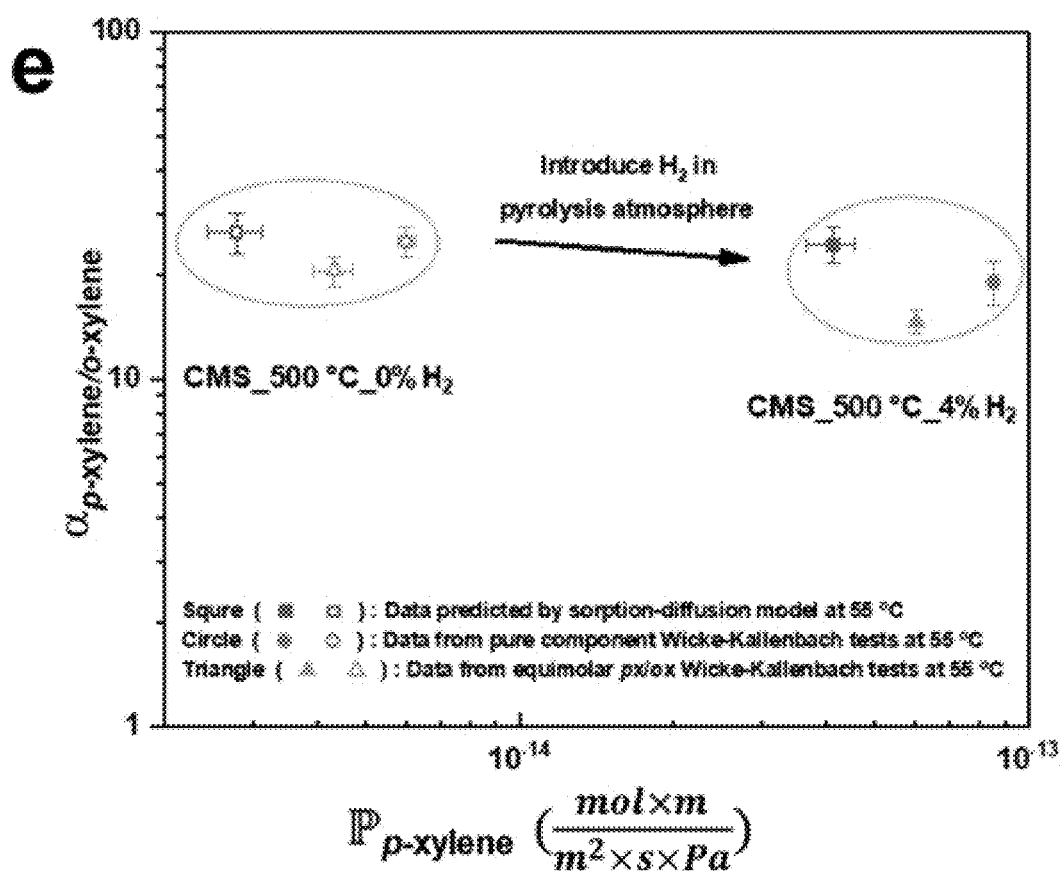

The surprising and beneficial effect of $H_2$ on the permeation performance of CMS membranes for the separation of xylene isomers is further illustrated in FIGS. 5D and 5E. To demonstrate the practical xylene separation performance of the CMS membranes, equimolar p-xylene/o-xylene mixed vapor permeation through these membranes were tested at 55° C. FIG. 5D shows the effect of hydrogen concentration and pyrolysis temperature on the p-xylene/o-xylene separation performances of CMS membranes based on equimolar Wicke-Kallenbach tests. It demonstrates that tightening of ultramicropores at decreasing $H_2$ amount or increasing pyrolysis temperatures improves discrimination of xylene isomers at the cost of permeability. FIG. 5E shows p-xylene/o-xylene separation performances of 4 vol. % $H_2$ assisted CMS membranes (solid) in comparison with those of membranes pyrolyzed under pure argon environment (hollow). As shown, the membranes prepared at 500° C. and 4 vol. % $H_2$/Ar gain at least 14 times larger p-xylene permeability than the membrane prepared without $H_2$, whether to sorption-diffusion model predicted permeability, to experimental ones from pure component Wicke-Kallenbach measurements or equimolar Wicke-Kallenbach measurements.

Accordingly, the larger ultramicropores generated with the help of $H_2$ provide less resistance to diffusion of guest molecules compared with the extremely narrow ultramicropores resulting from the pure argon pyrolysis. Unlike the permeability, the permselectivity can exhibit only negligible change. This is likely owing to the fact that the permselectivity is mainly dominated by the ultramicropores inside the CMS membrane and the size of the $H_2$ enlarged ultramicropores from around 5 to 7 Å (e.g. the xylene isomers used, p-xylene and o-xylene, have kinetic diameters of 5.8 Å and 6.8 Å, respectively). As a result, the $H_2$ assisted CMS can still effectively distinguish between p-xylene and o-xylene with molecular sieving effect provided by the rigid ultramicropores with the appropriate size. It should be noticed that for the pure component Wicke-Kallenbach tests, comparing with sorption-diffusion model predicted results, the permeability of p-xylene is higher $$\left(8.5 \times 10^{-14} \text{ vs. } 4.1 \times 10^{-14} \frac{mol \times m}{m^2 \times s \times Pa}\right)$$

and permselectivity is lower (e.g. 18.8 vs. 24.6). This might be contributed by some small, nonselective leak pathways inside the CMS membranes. The p-xylene permeability in the equimolar mixture test is smaller than the value obtained from the pure component test $$\left(6.0 \times 10^{-14} \text{ vs. } 8.5 \times 10^{-14} \frac{mol \times m}{m^2 \times s \times Pa}\right)$$

while the permselectivity decrease in the mixture case (e.g. 14.7 vs. 18.8) which is a signal of the frictional coupling effects between rapidly and slowly transporting xylene molecules.

Example 8: X-Ray Diffraction Analyses

X-ray diffraction (XRD) analyses were performed on a X'Pert PRO Alpha-1X-ray diffractometer with X' celerator detector and Cu Kα radiation (λ=1.5406 Å) at a voltage of 45 kV and current of 40 mA using the scanning angle 2θ from 5° to 600, at a step size of 0.016° and scan time of 20 s/step.

Figure 6A:
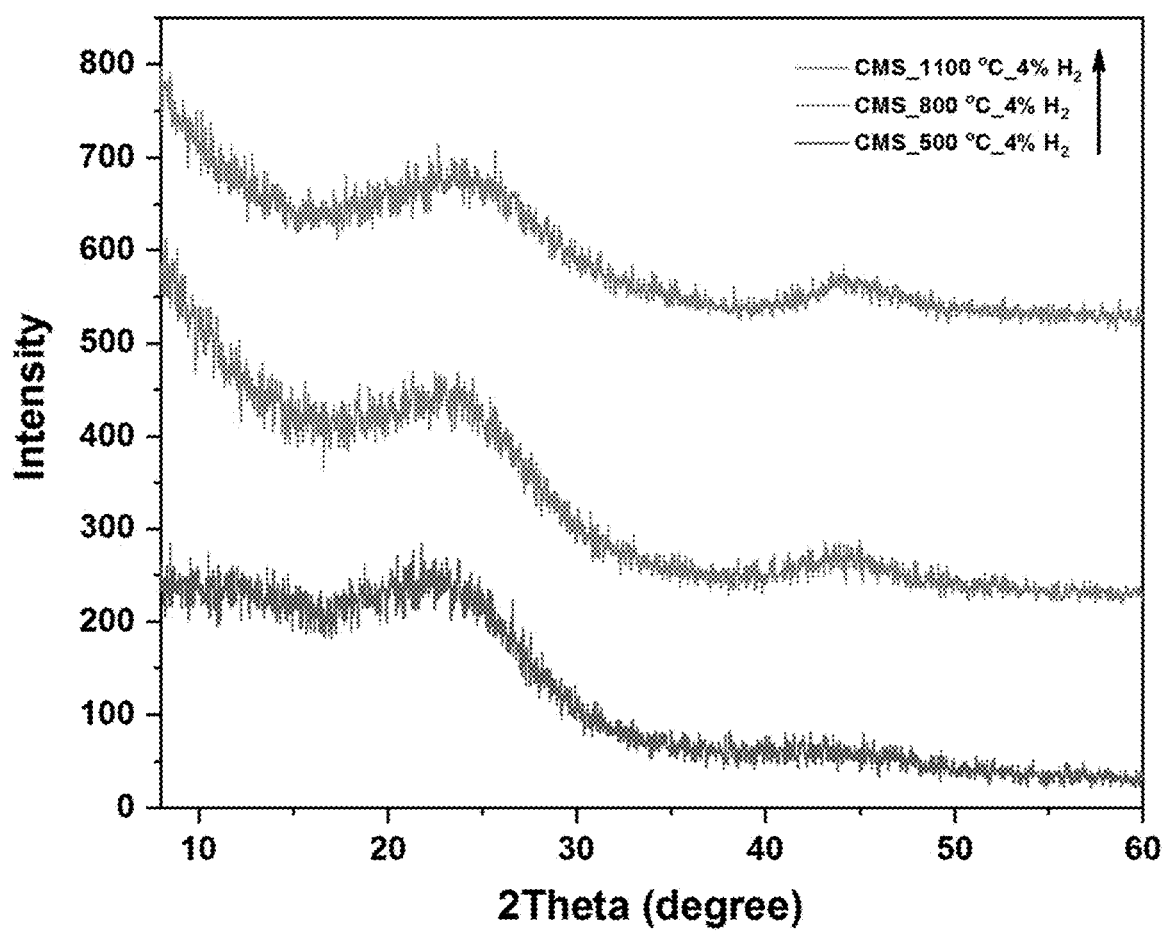
FIGS. 6A-6B depict X-ray diffraction analyses in accordance with various embodiments of this disclosure.
Figure 6B:
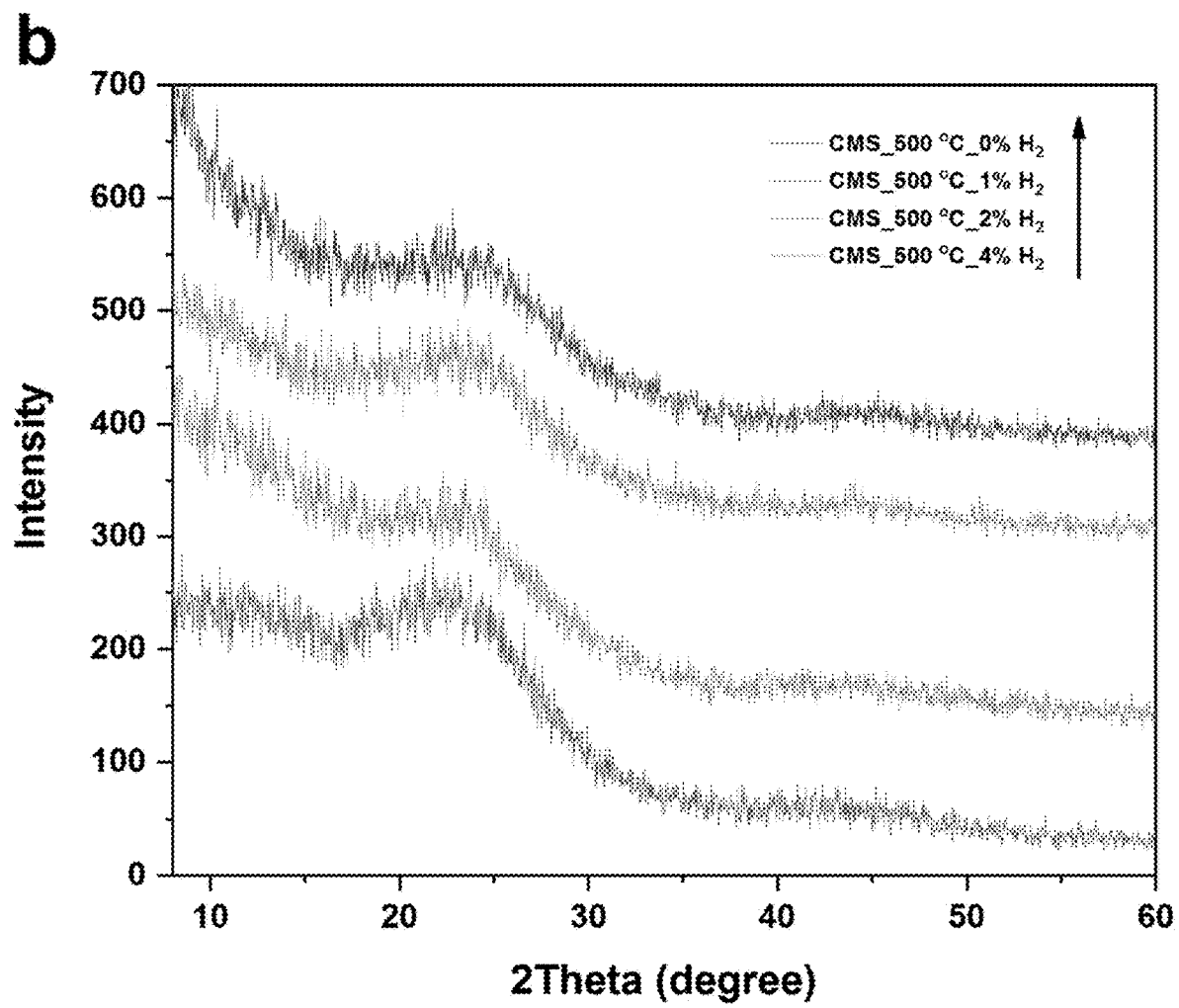

XRD data, shown in FIG. 6A, provides detailed information to investigate the d-spacing of CMS materials, which manifested as a broad reflection representing the average inter-planar distance between carbon sheets. As the slit-like micropores in CMS are formed by insufficient packing of adjacent carbon sheets, the inter-layer distance can be used to qualitatively assess the diffusional passageways for guest molecules. The detected broad reflections of the CMS membrane moved gradually from 22.7° to 23.8° with increase in pyrolysis temperature. The movement of the center position of reflections shown in XRD revealed that the interlayer spacing between adjacent planes reduced with increasing pyrolysis temperature. Particularly, the average d-spacing decreased from 3.91 Å to 3.74 Å, mainly determined by the difference in the condition of atomic organization and degree of carbonization for different pyrolysis temperatures. The decreased d-spacing values for the CMS materials indicated a lower free volume. In addition, the reflections observed around 44.0° were more pronounced at higher pyrolysis temperatures. This reflection, which reveals a d-spacing value of 2.06 Å, is the signal of the carbon-carbon spacing of the graphitic planes ((100) plane in ideal graphite), and reveals the formation of well packed and more ordered carbon structures in CMS. To some extent, this phenomenon demonstrates that the structure of the CMS membranes became more like that of ideal graphite at higher pyrolysis temperatures. The XRD results presented here, which support hypothesis of temperature-induced loss of porosity in CMS materials, agrees well with the results from CMS analogs derived from PIM-1. The effect of pyrolysis hydrogen concentration on XRD patterns was also studied as shown in FIG. 6B. The broad reflections moved gradually from 23.2° to 22.70 as the $H_2$ concentration increase from 0% to 4%, which means that average d-spacing increased from 3.83 Å to 3.91 Å. This also gives proof that $H_2$ can inhibit pore structure collapse during pyrolysis process.

Example 9: Fourier-Transform Infrared Spectra

Fourier-transform infrared spectra (FTIR) were recorded under transmittance mode on a Thermo Scientific Nicolet iS50 FT-IR spectrometer (Thermo Scientific, West Palm Beach, Fla.), where samples were ground with potassium bromide (KBr) in a mass ratio of 1:100 and pressed into a wafer. The range was set from 2400 to 800 $cm^{-1}$ with 64 scans and a resolution of 8 $cm^{-1}$.

Figure 7A:
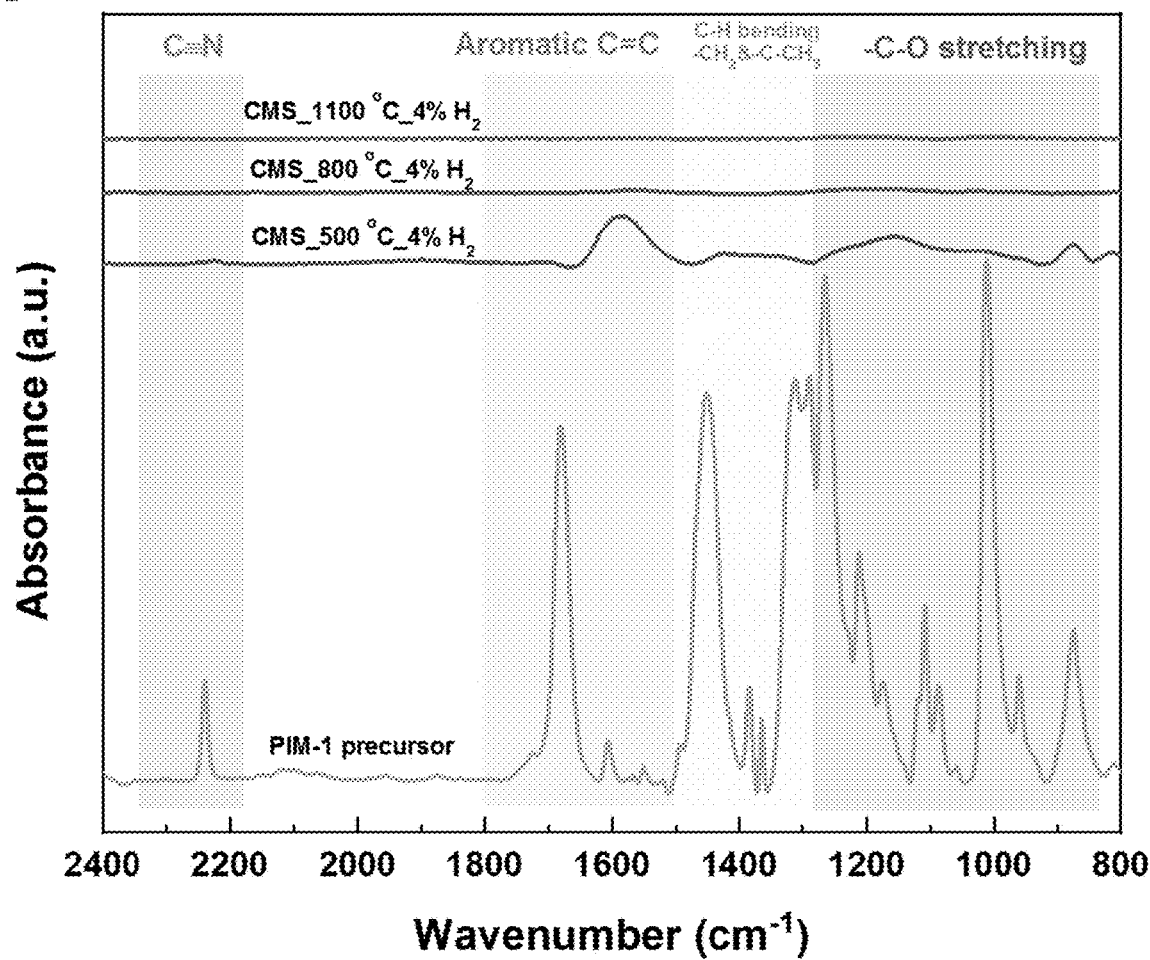
FIGS. 7A-7B depict Fourier-transform infrared spectra analyses in accordance with various embodiments of this disclosure.
Figure 7B:
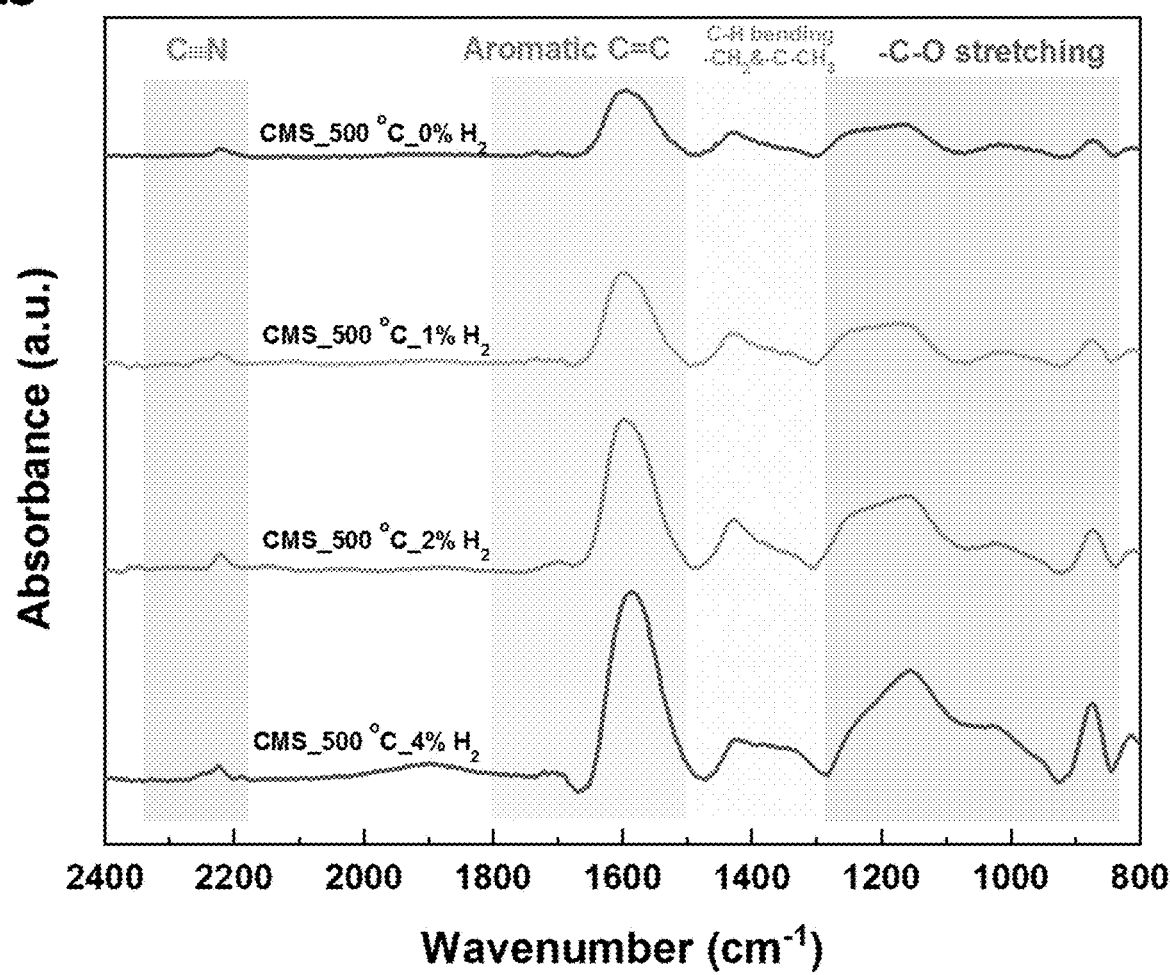

FTIR spectra, FIGS. 7A-7B, shows the chemical evolution of the carbonized PIM-1 as a function of pyrolysis temperature and $H_2$ amount. The spectrum of PIM-1 shows characteristic absorbance bands at 2238 $cm^{-1}$ (C≡N), 1607 $cm^{-1}$ (aromatic C=C bending), 1470-1430 $cm^{-1}$ (—C—H bending within —$CH_2$— and —C—$CH_3$ group) and 1300-1000 $cm^{-1}$ (—C—O— stretching). As shown in FIG. 7B, for CMS sample pyrolyzed at 500° C., even though the peak intensities of several bands reduce significantly compared with PIM-1 precursor, there are still obvious absorbance bands, which means CMS samples pyrolyzed at relative low temperatures retain some polymeric characteristics to some degree. However, as shown in FIG. 7A, absorbance bands disappeared as pyrolysis temperature further increased to 800° C. or even 1100° C. XRD results showed that CMS samples formed at higher pyrolysis temperatures are more graphite-like. It is worth noting that there are no functional groups presenting in the FTIR spectrum for ideal graphite. In addition, the peak intensities of characteristic bands increase obviously as the hydrogen concentration in the pyrolysis environment increases. This phenomenon suggests that the CMS samples pyrolyzed under higher $H_2$ amount condition, to some degree, are more polymeric like which is also proved by experiments about total sample weight loss after pyrolysis.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily used as a basis for the design of other structures, methods, and systems for carrying out the several purposes of the embodiments and claims presented in this application. It is important, therefore, that the claims be regarded as including such equivalent constructions.

What is claimed is:

1. A process for controlling a pore structure of a carbon molecular sieve comprising:
   providing a polymer precursor comprising a rigid microporous polymer;
   heating the polymer precursor in a chamber to at least a temperature at which the polymer precursor undergoes pyrolysis; and
   flowing a reactive gas stream through the chamber during the heating to control the pore structure of the carbon molecular sieve,
   wherein the reactive gas stream comprises $H_2$ and the carbon molecular sieve comprising the polymer precursor.

2. The process of claim 1, wherein the reactive gas stream further comprises an inert gas selected from a group consisting of argon, neon, $N_2$, helium, and $CO_2$ or combinations thereof.

3. The process of claim 1, wherein the reactive gas stream further comprises argon.

4. The process of claim 1, wherein the temperature of the pyrolysis of the polymer precursor film is from 500° C. to 1500° C.

5. The process of claim 1, wherein soak time of the pyrolysis of the polymer precursor film is from 30 min to 24 hours.

6. The process of claim 1, wherein the reactive gas stream is a pure $H_2$ stream.

7. The process of claim 1, wherein the $H_2$ is in a concentration of from 1 ppm to 4 vol. % of the reactive gas stream.

8. The process of claim 1, wherein the polymer precursor comprises a rigid polymer.

9. The process of claim 1, wherein the rigid microporous polymer is a polymer of intrinsic microporosity selected from a group consisting of PIM-1, PIM-7, PIM-8, PIM-9, KAUST-PI-1, PIM-BADAS-1, PIM-DUCKY-1, PIM-$Tz_{25}$, PIM-DUCKY-2, PIM-BADAS-2, PIM-SADAS, and combinations thereof.

10. The process of claim 1, wherein the carbon molecular sieve is utilized as a membrane, adsorbent, catalyst, composite or a filter.

11. The process of claim 1, wherein the polymer precursor has a form factor of film, sheet fiber, hollow fiber, coated tube, coated disc, or coated monolith.

12. The process of claim 1, wherein an inert gas stream flows through the chamber during the heating, wherein the inert gas stream comprises argon, and wherein flow rate of the inert gas stream is different from flow rate of the reactive gas stream.

13. The process of claim 1, wherein the polymer precursor comprises PIM-1.

14. The process of claim 1, wherein ramp rate of the process is from 0.1° C./min to 200° C./min.

15. The process of claim 1, wherein cool down rate of the process is from 0.1° C./min to 200° C./min.

16. The process of claim 1, wherein the reactive gas stream reacts with the polymer precursor to form $H_2O$ and/or $CO_2$ during pyrolysis.

17. The process of claim 1, wherein the chamber comprises a fume hood comprising a tubular furnace, a quartz tube disposed at least partially inside of the tubular furnace, a mesh plate support disposed inside of the quartz tube, and the polymer precursor is disposed on the mesh plate support.

18. The process of claim 1, wherein ultra-micropores of the carbon molecular sieve are selectively targeted by the pyrolysis to prevent collapse while leaving the micropores relatively unchanged.

19. The process of claim 1, wherein the diffusion selectivity of the polymer precursor is enhanced while the sorption selectivity of the polymer precursor is essentially unchanged.

20. The process of claim 1, wherein an $H_2$ concentration and/or pyrolysis temperature is selected to obtain a desired molecule permeance or perm-selectivity.

21. The process of claim 1, wherein the polymer precursor is heated in a stepwise manner during the heating step.

22. The process of claim 1, wherein the rigid microporous polymer is a polymer of intrinsic microporosity selected from a group consisting of PIM-8, PIM-9, KAUST-PI-1, PIM-BADAS-1, PIM-DUCKY-1, PIM-Tz$_{25}$, PIM-DUCKY-2, PIM-BADAS-2, PIM-SADAS, and combinations thereof.

\* \* \* \* \*